(12) United States Patent
Hoffmann et al.

(10) Patent No.: US 6,767,887 B1
(45) Date of Patent: Jul. 27, 2004

(54) EXENDIN ANALOGUES, PROCESSES FOR THEIR PREPARATION AND MEDICAMENTS CONTAINING THEM

(75) Inventors: Eike Hoffmann, Viernheim (DE); Rüdiger Göke, Marburg (DE); Burkhard-Johannes Göke, Marburg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/147,345
(22) PCT Filed: Jun. 5, 1997
(86) PCT No.: PCT/EP97/02930
§ 371 (c)(1),
(2), (4) Date: Jun. 4, 1999
(87) PCT Pub. No.: WO97/46584
PCT Pub. Date: Dec. 11, 1997

(51) Int. Cl.$^7$ .......................... A61K 38/16; C07K 7/00
(52) U.S. Cl. ........................... 514/2; 514/866; 530/324
(58) Field of Search ...................... 514/2, 866; 530/324

(56) References Cited

U.S. PATENT DOCUMENTS 5,424,286 A  *  6/1995  Eng ............................. 514/2

* cited by examiner

*Primary Examiner*—Bennett Celsa
(74) *Attorney, Agent, or Firm*—Rothwell, Figg, Ernst & Manbeck, P.C.

(57) ABSTRACT

The invention concerns exendin analogues which can be used in the treatment of diabetes mellitus. The invention also concerns processes for preparing these substances and medicaments containing them. The exendin analogues are derived from SEQ ID:1(I) or SEQ ID:2(II).

54 Claims, No Drawings

SEQUENCE LISTING (1) GENERAL INFORMATION:

(iii) NUMBER OF SEQUENCES: 120

(2) INFORMATION FOR SEQ ID NO: 1:

(i) SEQUENCE CHARACTERISTICS:
      (A) LENGTH: 30 amino acids
      (B) TYPE: amino acid
      (C) STRANDEDNESS: single strand
      (D) TOPOLOGY: linear (ii) MOLECULE TYPE: peptide (ix) FEATURE:
      (A) NAME/KEY: peptide
      (B) LOCATION:30
      (D) OTHER INFORMATION:/product= "Xaa denotes
          all amino acids except for Gly"

(xi) SEQUENCE DESCRIPTION: SEQ ID NO: 1:

```
His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Xaa
            20                  25                  30
```

(2) INFORMATION FOR SEQ ID NO: 2:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:30
        (D) OTHER INFORMATION:/product= "Xaa denotes
            all amino acids except for Gly"

(xi) SEQUENCE DESCRIPTION: SEQ ID NO: 2:

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Xaa
            20                  25                  30
```

(2) INFORMATION FOR SEQ ID NO: 3:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 3:

```
His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30
```

(2) INFORMATION FOR SEQ ID NO: 4:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 4:

```
His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Tyr
            20                  25                  30
```

(2) INFORMATION FOR SEQ ID NO: 5:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 5:

His Ser Asp Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 6:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 6:

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 7:

(i) SEQUENCE CHARACTERISTICS:
        (A) LENGTH: 29 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:13
        (D) OTHER INFORMATION:/product= "Xaa denotes Nle"

(xi) SEQUENCE DESCRIPTION: SEQ ID NO: 7:

Gly Glu Gly Thr Phe Thr Ser Asp Leu Ser Lys Gln Xaa Glu Glu Glu
1               5                   10                  15

Ala Val Arg Leu Phe Ile Glu Trp Leu Lys Asn Gly Arg
            20                  25

(2) INFORMATION FOR SEQ ID NO: 8:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 8:

His Gly Glu Gly Thr Phe Thr Ser Asp Leu Ser Lys Gln Met Glu Glu
1               5                   10                  15

Glu Ala Val Arg Ala Phe Ile Glu Trp Leu Lys Asn Gly Arg
            20                  25                  30

(2) INFORMATION FOR SEQ ID NO: 9:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 9:

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Ala Gly Arg
            20                  25                  30

(2) INFORMATION FOR SEQ ID NO: 10:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 10:

His Gly Glu Gly Thr Phe Thr Ser Asp Leu Ser Lys Gln Met Glu Glu
1               5                   10                  15

Glu Ala Val Arg Ala Phe Ile Glu Trp Leu Lys Ala Gly Arg
            20                  25                  30

(2) INFORMATION FOR SEQ ID NO: 11:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: misc_feature
        (B) LOCATION: 30
        (D) OTHER INFORMATION:/product= "-OH replaces terminal -NH2"

(xi) SEQUENCE DESCRIPTION: SEQ ID NO: 11:

His Gly Glu Gly Thr Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 12:

(i) SEQUENCE CHARACTERISTICS:
        (A) LENGTH: 30 amino acids
        (B) TYPE: amino acid
        (C) STRANDEDNESS: single strand
        (D) TOPOLOGY: linear

```
    (ii) MOLECULE TYPE: peptide (ix) FEATURE:
        (A) NAME/KEY: misc_feature
        (B) LOCATION: 1
        (D) OTHER INFORMATION:/product= "Modified by Ac"

(xi) SEQUENCE DESCRIPTION: SEQ ID NO: 12:

His Gly Glu Gly Thr Phe Thr Ser Asp Leu Ser Lys Gln Ile Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 13:

(i) SEQUENCE CHARACTERISTICS:
        (A) LENGTH: 27 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 13:

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys
            20                  25

(2) INFORMATION FOR SEQ ID NO: 14:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 14:

His Ser Asp Gly Thr Phe Thr Ser Asp Leu Ser Lys Gln Ala Glu Glu
1               5                   10                  15

Glu Ala Val Arg Leu Phe Ile Glu Trp Leu Lys Asn Ala Arg
            20                  25                  30

(2) INFORMATION FOR SEQ ID NO: 15:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 15

His Ser Asp Gly Thr Phe Thr Ser Asp Leu Ser Lys Gln Ala Glu Glu
1               5                   10                  15

Glu Ala Val Arg Leu Phe Ile Glu Trp Leu Ala Asn Gly Arg
            20                  25                  30

(2) INFORMATION FOR SEQ ID NO: 16:
```

```
    (i) SEQUENCE CHARACTERISTICS:
        (A) LENGTH: 30 amino acids
        (B) TYPE: amino acid
        (C)
        (D) TOPOLOGY: linear (ii) MOLECULE TYPE: peptide (xi) SEQUENCE DESCRIPTION: SEQ ID NO: 16:

His Ser Asp Gly Thr Phe Thr Ser Asp Leu Ser Lys Gln Ala Glu Glu
1               5                   10                  15

Glu Ala Val Arg Leu Phe Ile Glu Trp Ala Lys Asn Gly Arg
            20                  25                  30

(2) INFORMATION FOR SEQ ID NO: 17:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 17:

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 18:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 18:

His Cys Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 19:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
```

(D) OTHER INFORMATION:/product= "Xaa denotes Nle"

(xi) SEQUENCE DESCRIPTION: SEQ ID NO: 19:

His Asp Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 20:

(i) SEQUENCE CHARACTERISTICS:
       (A) LENGTH: 30 amino acids
       (B) TYPE: amino acid
       (C) STRANDEDNESS: single strand
       (D) TOPOLOGY: linear (ii) MOLECULE TYPE: peptide (ix) FEATURE:
       (A) NAME/KEY: peptide
       (B) LOCATION:14
       (D) OTHER INFORMATION:/product= "Xaa denotes Nle"

(xi) SEQUENCE DESCRIPTION: SEQ ID NO: 20:

His Glu Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 21:

(i) SEQUENCE CHARACTERISTICS:
       (A) LENGTH: 30 amino acids
       (B) TYPE: amino acid
       (C) STRANDEDNESS: single strand
       (D) TOPOLOGY: linear (ii) MOLECULE TYPE: peptide (ix) FEATURE:
       (A) NAME/KEY: peptide
       (B) LOCATION:14
       (D) OTHER INFORMATION:/product= "Xaa denotes Nle"

(xi) SEQUENCE DESCRIPTION: SEQ ID NO: 21:

His Phe Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 22:

(i) SEQUENCE CHARACTERISTICS:
       (A) LENGTH: 30 amino acids
       (B) TYPE: amino acid
       (C) STRANDEDNESS: single strand
       (D) TOPOLOGY: linear (ii) MOLECULE TYPE: peptide (ix) FEATURE:
       (A) NAME/KEY: peptide
       (B) LOCATION:14
       (D) OTHER INFORMATION:/product= "Xaa denotes Nle"

(xi) SEQUENCE DESCRIPTION: SEQ ID NO: 22:

His His Glu Gly Thr Phe Thr Ser Asp Leu Ser Lys Gln Xaa Glu Glu
1               5                   10                  15

```
Glu Ala Val Arg Leu Phe Ile Glu Trp Leu Lys Asn Gly Arg
            20                  25                  30

(2) INFORMATION FOR SEQ ID NO: 23:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 23:

His Ile Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 24:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 24:

His Lys Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 25:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 25:

His Leu Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 26:

(i) SEQUENCE CHARACTERISTICS:
```

(A) LENGTH: 30 amino acids
       (B) TYPE: amino acid
       (C) STRANDEDNESS: single strand
       (D) TOPOLOGY: linear (ii) MOLECULE TYPE: peptide (ix) FEATURE:
       (A) NAME/KEY: peptide
       (B) LOCATION:14
       (D) OTHER INFORMATION:/product= "Xaa denotes Nle"

(xi) SEQUENCE DESCRIPTION: SEQ ID NO: 26:

His Met Glu Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 27:

(i) SEQUENCE CHARACTERISTICS:
       (A) LENGTH: 30 amino acids
       (B) TYPE: amino acid
       (C) STRANDEDNESS: single strand
       (D) TOPOLOGY: linear (ii) MOLECULE TYPE: peptide (ix) FEATURE:
       (A) NAME/KEY: peptide
       (B) LOCATION:14
       (D) OTHER INFORMATION:/product= "Xaa denotes Nle"

(xi) SEQUENCE DESCRIPTION: SEQ ID NO: 27:

His Asn Glu Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 28:

(i) SEQUENCE CHARACTERISTICS:
       (A) LENGTH: 30 amino acids
       (B) TYPE: amino acid
       (C) STRANDEDNESS: single strand
       (D) TOPOLOGY: linear (ii) MOLECULE TYPE: peptide (ix) FEATURE:
       (A) NAME/KEY: peptide
       (B) LOCATION:14
       (D) OTHER INFORMATION:/product= "Xaa denotes Nle"

(xi) SEQUENCE DESCRIPTION: SEQ ID NO: 28:

His Pro Glu Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 29:

(i) SEQUENCE CHARACTERISTICS:
       (A) LENGTH: 30 amino acids
       (B) TYPE: amino acid
       (C) STRANDEDNESS: single strand
       (D) TOPOLOGY: linear (ii) MOLECULE TYPE: peptide

```
   (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 29:

His Gln Glu Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 30:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 30:

His Arg Glu Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 31:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 31:

His Ser Glu Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 32:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 32:
```

```
His Thr Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30
```

(2) INFORMATION FOR SEQ ID NO: 33:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 33:

```
His Val Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30
```

(2) INFORMATION FOR SEQ ID NO: 34:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 34:

```
His Trp Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30
```

(2) INFORMATION FOR SEQ ID NO: 35:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 35:

```
His Tyr Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30
```

```
(2) INFORMATION FOR SEQ ID NO: 36:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 36:

His Ala Asp Gly Thr Phe Thr Ser Asp Leu Ser Ser Tyr Met Glu Gly
1               5                   10                  15

Gln Ala Val Lys Glu Phe Ile Ala Trp Leu Val Lys Gly Arg
            20                  25                  30

(2) INFORMATION FOR SEQ ID NO: 37:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 37:

His Ser Asp Gly Thr Phe Thr Ser Asp Leu Ser Lys Gln Ala Glu Glu
1               5                   10                  15

Glu Ala Val Arg Leu Phe Ile Glu Ala Leu Lys Asn Gly Arg
            20                  25                  30

(2) INFORMATION FOR SEQ ID NO: 38:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 38:

His Ser Glu Gly Thr Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 39:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 39:

Ala Ser Asp Gly Thr Phe Thr Ser Asp Leu Ser Lys Gln Val Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 40:

(i) SEQUENCE CHARACTERISTICS:
```

(A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 40:

His Gly Ala Gly Thr Phe Thr Ser Asp Leu Ser Lys Gln Ala Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 41:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 41:

His Gly Glu Gly Ala Phe Thr Ser Asp Leu Ser Lys Gln Ala Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 42:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 42:

His Gly Glu Gly Tyr Phe Thr Ser Asp Leu Ser Lys Gln Ala Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 43:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 43:

His Gly Glu Gly Thr Tyr Thr Ser Asp Leu Ser Lys Gln Ala Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 44:

(i) SEQUENCE CHARACTERISTICS:
            (A) LENGTH: 30 amino acids
            (B) TYPE: amino acid
            (C) STRANDEDNESS: single strand

```
         (D) TOPOLOGY: linear (ii) MOLECULE TYPE: peptide (xi) SEQUENCE DESCRIPTION: SEQ ID NO: 44:

His Gly Glu Gly Thr Ile Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 45:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 45:

His Gly Glu Gly Thr Phe Ser Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 46:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 46:

His Gly Glu Gly Thr Phe Tyr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 47:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 47:

His Gly Glu Gly Thr Phe Thr Thr Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 48:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide
```

(xi) SEQUENCE DESCRIPTION: SEQ ID NO: 48:

His Gly Glu Gly Thr Phe Thr Tyr Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 49:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 49:

His Gly Glu Gly Thr Phe Thr Ser Glu Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 50:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 50:

His Gly Glu Gly Thr Phe Thr Ser Asp Ala Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 51:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 51:

His Gly Glu Gly Thr Phe Thr Ser Asp Leu Ala Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 52:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 52:

```
His Gly Glu Gly Thr Phe Thr Ser Asp Leu Ser Ala Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 53:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 53:

His Gly Glu Gly Thr Phe Thr Ser Asp Leu Ser Lys Ala Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 54:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 54:

His Gly Glu Gly Thr Phe Thr Ser Asp Leu Ser Lys Gln Ala Ala Glu
1               5                   10                  15

Glu Ala Val Arg Leu Phe Ile Glu Trp Leu Lys Asn Gly Arg
            20                  25                  30

(2) INFORMATION FOR SEQ ID NO: 55:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 55:

Gly Ser Asp Gly Ser Phe Thr Ser Asp Leu Ser Lys Gln Ala Glu Ala
1               5                   10                  15

Glu Ala Val Arg Leu Phe Ile Glu Trp Leu Lys Asn Gly Arg
            20                  25                  30

(2) INFORMATION FOR SEQ ID NO: 56:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 56:

Lys Gly Glu Gly Thr Phe Thr Ser Asp Leu Ser Lys Gln Ala Glu Glu
1               5                   10                  15
```

```
Ala Ala Val Arg Leu Phe Ile Glu Trp Leu Lys Asn Gly Arg
            20                  25                  30

(2) INFORMATION FOR SEQ ID NO: 57:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 57:

His Gly Glu Gly Thr Phe Thr Ser Asp Leu Ser Lys Gln Ala Glu Glu
1               5                   10                  15

Glu Leu Val Arg Leu Phe Ile Glu Trp Leu Lys Asn Gly Arg
            20                  25                  30

(2) INFORMATION FOR SEQ ID NO: 58:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 58:

His Gly Glu Gly Thr Phe Thr Ser Asp Leu Ser Lys Gln Ala Glu Glu
1               5                   10                  15

Glu Ala Ile Arg Leu Phe Ile Glu Trp Leu Lys Asn Gly Arg
            20                  25                  30

(2) INFORMATION FOR SEQ ID NO: 59:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 59:

His Gly Glu Gly Thr Phe Thr Ser Asp Leu Ser Lys Gln Ala Glu Glu
1               5                   10                  15

Glu Ala Val Ala Leu Phe Ile Glu Trp Leu Lys Asn Gly Arg
            20                  25                  30

(2) INFORMATION FOR SEQ ID NO: 60:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 60:

His Ser Asp Gly Thr Phe Thr Ser Asp Leu Ser Lys Gln Ala Glu Glu
1               5                   10                  15

Glu Ala Val Arg Leu Tyr Ile Glu Trp Leu Lys Asn Gly Arg
            20                  25                  30
```

(2) INFORMATION FOR SEQ ID NO: 61:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 61:

```
His Gly Glu Gly Thr Phe Thr Ser Asp Leu Ser Lys Gln Ala Glu Glu
1               5                   10                  15

Glu Ala Val Arg Leu Phe Val Glu Trp Leu Lys Asn Gly Arg
            20                  25                  30
```

(2) INFORMATION FOR SEQ ID NO: 62:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 62:

```
His Gly Glu Gly Thr Phe Thr Ser Asp Leu Ser Lys Gln Ala Glu Glu
1               5                   10                  15

Glu Ala Val Arg Leu Phe Ile Leu Trp Leu Lys Asn Gly Arg
            20                  25                  30
```

(2) INFORMATION FOR SEQ ID NO: 63:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 63:

```
His Gly Glu Gly Thr Phe Thr Ser Asp Leu Ser Lys Gln Ala Glu Glu
1               5                   10                  15

Glu Ala Val Arg Leu Phe Ile Glu Ala Leu Lys Asn Gly Arg
            20                  25                  30
```

(2) INFORMATION FOR SEQ ID NO: 64:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 64:

```
His Gly Glu Gly Thr Phe Thr Ser Asp Leu Ser Lys Gln Ala Glu Glu
1               5                   10                  15

Glu Ala Val Arg Leu Phe Ile Glu Trp Ala Lys Asn Gly Arg
            20                  25                  30
```

(2) INFORMATION FOR SEQ ID NO: 65:

```
     (i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 65:

His Gly Glu Gly Thr Phe Thr Ser Asp Leu Ser Lys Gln Ala Glu Glu
1               5                   10                  15

Glu Ala Val Arg Leu Phe Ile Glu Trp Leu Ala Asn Gly Arg
            20                  25                  30

(2) INFORMATION FOR SEQ ID NO: 66:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 66:

His Gly Glu Gly Thr Phe Thr Ser Asp Leu Ser Lys Gln Ala Glu Glu
1               5                   10                  15

Glu Ala Val Arg Leu Phe Ile Glu Trp Leu Lys Asn Ala Arg
            20                  25                  30

(2) INFORMATION FOR SEQ ID NO: 67:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 67:

His Gly Glu Gly Thr Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 68:

(i) SEQUENCE CHARACTERISTICS:
         (A) LENGTH: 30 amino acids
         (B) TYPE: amino acid
         (C) STRANDEDNESS: single strand
         (D) TOPOLOGY: linear (ii) MOLECULE TYPE: peptide (xi) SEQUENCE DESCRIPTION: SEQ ID NO: 68:

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 69:

(i) SEQUENCE CHARACTERISTICS:
         (A) LENGTH: 30 amino acids
         (B) TYPE: amino acid
```

```
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 69:

His Ser Asp Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Tyr
            20                  25                  30

(2) INFORMATION FOR SEQ ID NO: 70:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(ix) FEATURE:
        (A) NAME/KEY: misc_feature
        (B) LOCATION: 30
        (D) OTHER INFORMATION:/product= "-OH replaces terminal -NH2"

(xi) SEQUENCE DESCRIPTION: SEQ ID NO: 70:

His Ser Asp Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 71:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 71:

His Ser Asp Gly Thr Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 72:

(i) SEQUENCE CHARACTERISTICS:
        (A) LENGTH: 29 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
```

(B) LOCATION:13
        (D) OTHER INFORMATION:/product= "Xaa denotes Nle"

(xi) SEQUENCE DESCRIPTION: SEQ ID NO: 72:

Ser Asp Gly Thr Phe Thr Ser Asp Leu Ser Lys Gln Xaa Glu Glu Glu
1               5                   10                  15

Ala Val Arg Leu Phe Ile Glu Trp Leu Lys Asn Gly Arg
            20                  25

(2) INFORMATION FOR SEQ ID NO: 73:

(i) SEQUENCE CHARACTERISTICS:
        (A) LENGTH: 28 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:12
        (D) OTHER INFORMATION:/product= "Xaa denotes Nle"

(xi) SEQUENCE DESCRIPTION: SEQ ID NO: 73:

Asp Gly Thr Phe Thr Ser Asp Leu Ser Lys Gln Xaa Glu Glu Glu Ala
1               5                   10                  15

Val Arg Leu Phe Ile Glu Trp Leu Lys Asn Gly Arg
            20                  25

(2) INFORMATION FOR SEQ ID NO: 74:

(i) SEQUENCE CHARACTERISTICS:
        (A) LENGTH: 29 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: misc_feature
        (B) LOCATION: 1
        (D) OTHER INFORMATION:/product= "Modified by Ac"

(ix) FEATURE:
        (A) NAME/KEY: peptide
        (B) LOCATION:13
        (D) OTHER INFORMATION:/product= "Xaa denotes Nle"

(xi) SEQUENCE DESCRIPTION: SEQ ID NO: 74:

Ser Asp Gly Thr Phe Thr Ser Asp Leu Ser Lys Gln Xaa Glu Glu Glu
1               5                   10                  15

Ala Val Arg Leu Phe Ile Glu Trp Leu Lys Asn Gly Arg
            20                  25

(2) INFORMATION FOR SEQ ID NO: 75:

(i) SEQUENCE CHARACTERISTICS:
        (A) LENGTH: 28 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: misc_feature
        (B) LOCATION: 1
        (D) OTHER INFORMATION:/product= "Modified by Ac"

```
        (ix) FEATURE:
              (A) NAME/KEY: peptide
              (B) LOCATION:12
              (D) OTHER INFORMATION:/product= "Xaa denotes Nle"

(xi) SEQUENCE DESCRIPTION: SEQ ID NO: 75:

Asp Gly Thr Phe Thr Ser Asp Leu Ser Lys Gln Xaa Glu Glu Glu Ala
1               5                  10                  15

Val Arg Leu Phe Ile Glu Trp Leu Lys Asn Gly Arg
            20                  25

(2) INFORMATION FOR SEQ ID NO: 76:

(i) SEQUENCE CHARACTERISTICS:
              (A) LENGTH: 27 amino acids
              (B) TYPE: amino acid
              (C) STRANDEDNESS: single strand
              (D) TOPOLOGY: linear (ii) MOLECULE TYPE: peptide (ix) FEATURE:
              (A) NAME/KEY: peptide
              (B) LOCATION:14
              (D) OTHER INFORMATION:/product= "Xaa denotes Nle"

(xi) SEQUENCE DESCRIPTION: SEQ ID NO: 76:

His Ser Asp Gly Thr Phe Thr Ser Asp Leu Ser Lys Gln Xaa Glu Glu
1               5                  10                  15

Glu Ala Val Arg Leu Phe Ile Glu Trp Leu Lys
            20                  25

(2) INFORMATION FOR SEQ ID NO: 77:

(i) SEQUENCE CHARACTERISTICS:
              (A) LENGTH: 30 amino acids
              (B) TYPE: amino acid
              (C) STRANDEDNESS: single strand
              (D) TOPOLOGY: linear (ii) MOLECULE TYPE: peptide (xi) SEQUENCE DESCRIPTION: SEQ ID NO: 77:

His Lys Pro Gly Thr Phe Thr Ser Asp Leu Ser Lys Gln Ala Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 78:

(i) SEQUENCE CHARACTERISTICS:
              (A) LENGTH: 30 amino acids
              (B) TYPE: amino acid
              (C) STRANDEDNESS: single strand
              (D) TOPOLOGY: linear (ii) MOLECULE TYPE: peptide (ix) FEATURE:
              (A) NAME/KEY: peptide
              (B) LOCATION:14
              (D) OTHER INFORMATION:/product= "Xaa denotes Nle"

(xi) SEQUENCE DESCRIPTION: SEQ ID NO: 78:

His Ala Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
```

```
            20                  25                  30

(2) INFORMATION FOR SEQ ID NO: 79:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 79:

His Cys Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 80:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 80:

His Asp Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 81:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 81:

His Glu Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 82:

(i) SEQUENCE CHARACTERISTICS:
        (A) LENGTH: 30 amino acids
```

(B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 82:

His Phe Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 83:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 83:

His Gly Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 84:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 84:

His His Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 85:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:

```
              (A) NAME/KEY: peptide
              (B) LOCATION:14
              (D) OTHER INFORMATION:/product= "Xaa denotes Nle"

(xi) SEQUENCE DESCRIPTION: SEQ ID NO: 85:

His Ile Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 86:

(i) SEQUENCE CHARACTERISTICS:
              (A) LENGTH: 30 amino acids
              (B) TYPE: amino acid
              (C) STRANDEDNESS: single strand
              (D) TOPOLOGY: linear (ii) MOLECULE TYPE: peptide (ix) FEATURE:
              (A) NAME/KEY: peptide
              (B) LOCATION:14
              (D) OTHER INFORMATION:/product= "Xaa denotes Nle"

(xi) SEQUENCE DESCRIPTION: SEQ ID NO: 86:

His Lys Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 87:

(i) SEQUENCE CHARACTERISTICS:
              (A) LENGTH: 30 amino acids
              (B) TYPE: amino acid
              (C) STRANDEDNESS: single strand
              (D) TOPOLOGY: linear (ii) MOLECULE TYPE: peptide (ix) FEATURE:
              (A) NAME/KEY: peptide
              (B) LOCATION:14
              (D) OTHER INFORMATION:/product= "Xaa denotes Nle"

(xi) SEQUENCE DESCRIPTION: SEQ ID NO: 87:

His Leu Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 88:

(i) SEQUENCE CHARACTERISTICS:
              (A) LENGTH: 30 amino acids
              (B) TYPE: amino acid
              (C) STRANDEDNESS: single strand
              (D) TOPOLOGY: linear (ii) MOLECULE TYPE: peptide (ix) FEATURE:
              (A) NAME/KEY: peptide
              (B) LOCATION:14
              (D) OTHER INFORMATION:/product= "Xaa denotes Nle"

(xi) SEQUENCE DESCRIPTION: SEQ ID NO: 88:

His Met Asp Gly Thr Phe Thr Ser Asp Leu Ser Lys Gln Xaa Glu Glu
```

```
                1               5                  10                 15
Glu Ala Val Arg Leu Phe Ile Glu Trp Leu Lys Asn Gly Arg
                20                 25                 30
```

(2) INFORMATION FOR SEQ ID NO: 89:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 89:

```
His Asn Asp Gly Thr Phe Thr Ser Asp Leu Ser Lys Gln Xaa Glu Glu
1               5                   10                  15
Glu Ala Val Arg Leu Phe Ile Glu Trp Leu Lys Asn Gly Arg
                20                  25                  30
```

(2) INFORMATION FOR SEQ ID NO: 90:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 90:

```
His Pro Asp Gly Thr Phe Thr Ser Asp Leu Ser Lys Gln Xaa Glu Glu
1               5                   10                  15
Glu Ala Val Arg Leu Phe Ile Glu Trp Leu Lys Asn Gly Arg
                20                  25                  30
```

(2) INFORMATION FOR SEQ ID NO: 91:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 91:

```
His Gln Asp Gly Thr Phe Thr Ser Asp Leu Ser Lys Gln Xaa Glu Glu
1               5                   10                  15
Glu Ala Val Arg Leu Phe Ile Glu Trp Leu Lys Asn Gly Arg
                20                  25                  30
```

(2) INFORMATION FOR SEQ ID NO: 92:

```
    (i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 92:

His Arg Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 93:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 93:

His Thr Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 94:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: peptide
        (B) LOCATION:14
        (D) OTHER INFORMATION:/product= "Xaa denotes Nle"

(xi) SEQUENCE DESCRIPTION: SEQ ID NO: 94:

His Val Asp Gly Thr Phe Thr Ser Asp Leu Ser Lys Gln Xaa Glu Glu
1               5                  10                  15

Glu Ala Val Arg Leu Phe Ile Glu Trp Leu Lys Asn Gly Arg
            20                  25                  30

(2) INFORMATION FOR SEQ ID NO: 95:

(i) SEQUENCE CHARACTERISTICS:
        (A) LENGTH: 30 amino acids
        (B) TYPE: amino acid
        (C) STRANDEDNESS: single strand
        (D) TOPOLOGY: linear
```

(ii) MOLECULE TYPE: peptide (ix) FEATURE:
            (A) NAME/KEY: peptide
            (B) LOCATION:14
            (D) OTHER INFORMATION:/product= "Xaa denotes Nle"

(xi) SEQUENCE DESCRIPTION: SEQ ID NO: 95:

His Trp Asp Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 96:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (ix) FEATURE:
            (A) NAME/KEY: peptide
            (B) LOCATION:14
            (D) OTHER INFORMATION:/product= "Xaa denotes Nle"

(xi) SEQUENCE DESCRIPTION: SEQ ID NO: 96:

His Tyr Asp Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 97:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 97:

His Ser Ala Gly Thr Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 98:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 98:

His Ser Asp Gly Ala Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 99:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 99:

His Ser Asp Gly Tyr Phe Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 100:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 100:

His Ser Asp Gly Thr Tyr Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 101:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 101:

His Ser Asp Gly Thr Ile Thr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 102:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 102:

His Ser Asp Gly Thr Phe Ser Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 103:

(i) SEQUENCE CHARACTERISTICS:
            (A) LENGTH: 30 amino acids (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 103:

His Ser Asp Gly Thr Phe Tyr Ser Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 104:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 104:

His Ser Asp Gly Thr Phe Thr Thr Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 105:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 105:

His Ser Asp Gly Thr Phe Thr Tyr Asp Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 106:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 106:

His Ser Asp Gly Thr Phe Thr Ser Glu Leu Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 107:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (xi) SEQUENCE DESCRIPTION: SEQ ID NO: 107:

His Ser Asp Gly Thr Phe Thr Ser Asp Ala Ser Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 108:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 108:

His Ser Asp Gly Thr Phe Thr Ser Asp Leu Ala Lys Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 109:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 109:

His Gly Glu Gly Thr Phe Thr Ser Asp Leu Ser Ala Gln Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 110:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 110:

His Ser Asp Gly Thr Phe Thr Ser Asp Leu Ser Lys Ala Ala Glu Glu
1               5                   10                  15

Glu Ala Val Arg Leu Phe Ile Glu Trp Leu Lys Asn Gly Arg
            20                  25                  30

(2) INFORMATION FOR SEQ ID NO: 111:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 111:

His Ser Asp Gly Thr Phe Thr Ser Asp Leu Ser Lys Gln Ala Ala Glu
1               5                   10                  15

Glu Ala Val Arg Leu Phe Ile Glu Trp Leu Lys Asn Gly Arg
            20                  25                  30

(2) INFORMATION FOR SEQ ID NO: 112:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 112:

Lys Ser Asp Gly Thr Phe Thr Ser Asp Leu Ser Lys Gln Ala Glu Glu
1               5                   10                  15

Ala Ala Val Arg Leu Phe Ile Glu Trp Leu Lys Asn Gly Arg
            20                  25                  30

(2) INFORMATION FOR SEQ ID NO: 113:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 113:

His Ser Asp Gly Thr Phe Thr Ser Asp Leu Ser Lys Gln Ala Glu Glu
1               5                   10                  15

Glu Leu Val Arg Leu Phe Ile Glu Trp Leu Lys Asn Gly Arg
            20                  25                  30

(2) INFORMATION FOR SEQ ID NO: 114:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 114:

His Ser Asp Gly Thr Phe Thr Ser Asp Leu Ser Lys Gln Ala Glu Glu
1               5                   10                  15

Glu Ala Ile Arg Leu Phe Ile Glu Trp Leu Lys Asn Gly Arg
            20                  25                  30

(2) INFORMATION FOR SEQ ID NO: 115:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 115:

His Ser Asp Gly Thr Phe Thr Ser Asp Leu Ser Lys Gln Ala Glu Glu

```
                1               5                    10                   15
Glu Ala Val Ala Leu Phe Ile Glu Trp Leu Lys Asn Gly Arg
                20                   25                   30

(2) INFORMATION FOR SEQ ID NO: 116:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 116:

His Ser Asp Gly Thr Phe Thr Ser Asp Leu Ser Lys Gln Ala Glu Glu
1               5                    10                   15
Glu Ala Val Arg Leu Tyr Ile Glu Trp Leu Lys Asn Gly Arg
                20                   25                   30

(2) INFORMATION FOR SEQ ID NO: 117:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 117:

His Ser Asp Gly Thr Phe Thr Ser Asp Leu Ser Lys Gln Ala Glu Glu
1               5                    10                   15
Glu Ala Val Arg Leu Phe Val Glu Trp Leu Lys Asn Gly Arg
                20                   25                   30

(2) INFORMATION FOR SEQ ID NO: 118:

(i) SEQUENCE CHARACTERISTICS:
        (A) LENGTH: 30 amino acids
        (B) TYPE: amino acid
        (C) STRANDEDNESS: single strand
        (D) TOPOLOGY: linear (ii) MOLECULE TYPE: peptide (xi) SEQUENCE DESCRIPTION: SEQ ID NO: 118:

His Ser Asp Gly Thr Phe Thr Ser Asp Leu Ser Lys Gln Ala Glu Glu
1               5                    10                   15
Glu Ala Val Arg Leu Phe Ile Leu Trp Leu Lys Asn Gly Arg
                20                   25                   30

(2) INFORMATION FOR SEQ ID NO: 119:

(i) SEQUENCE CHARACTERISTICS:
        (A) LENGTH: 28 amino acids
        (B) TYPE: amino acid
        (C) STRANDEDNESS: single strand
        (D) TOPOLOGY: linear (ii) MOLECULE TYPE: peptide (ix) FEATURE:
        (A) NAME/KEY: misc_feature
        (B) LOCATION: 1
        (D) OTHER INFORMATION:/product= "Modified by Suc"

(ix) FEATURE:
```

```
            (A) NAME/KEY: peptide
            (B) LOCATION:12
            (D) OTHER INFORMATION:/product= "Xaa denotes Nle"

(xi) SEQUENCE DESCRIPTION: SEQ ID NO: 119:

Asp Gly Thr Phe Thr Ser Asp Leu Ser Lys Gln Xaa Glu Glu Glu Ala
1               5                   10                  15

Val Arg Leu Phe Ile Glu Trp Leu Lys Asn Gly Arg
            20                  25

(2) INFORMATION FOR SEQ ID NO: 120:

(i) SEQUENCE CHARACTERISTICS:
            (A) LENGTH: 30 amino acids
            (B) TYPE: amino acid
            (C) STRANDEDNESS: single strand
            (D) TOPOLOGY: linear (ii) MOLECULE TYPE: peptide (ix) FEATURE:
            (A) NAME/KEY: peptide
            (B) LOCATION:14
            (D) OTHER INFORMATION:/product= "Xaa denotes Nle"

(xi) SEQUENCE DESCRIPTION: SEQ ID NO: 120:

His Ser Asp Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Arg
            20                  25                  30
```

EXENDIN ANALOGUES, PROCESSES FOR THEIR PREPARATION AND MEDICAMENTS CONTAINING THEM

This application is a 371 of PCT/EP97/02930 filed Jun. 5, 1997 claiming priority to DE 196 22 502.7 filed Jun. 5, 1996 and DE 196 37 230.5 filed Sep. 13, 1996.

This invention concerns new exendin analogues which can be used in the therapy of diabetes mellitus, processes for their production and pharmaceutical preparations containing them.

BACKGROUND OF THE INVENTION

A functional connection between the small intestine and exocrine pancreas was proven in the 1960's after it became possible to accurately determine insulin in plasma. The insulin response after oral glucose administration is much stronger than after intravenous glucose administration even if identical plasma levels of glucose are reached. This "incretin effect" is explained by the functional combination of the entero-insular axis. Intestinal hormones are responsible for this effect which are released from the small intestine after meals, circulate in the plasma at increased measurable levels and amplify glucose-induced insulin release. In addition to the classical incretin hormone gastric inhibitory polypeptide I (GIP), glucagon-like peptide. 1 (GLP-1) is nowadays of primary interest. In a relatively short time GLP-1 has matured from being the physiologically most interesting incretin hormone candidate to a potential alternative for the treatment of diabetes mellitus type II. The present invention describes new substances which imitate the effect of the naturally occurring GLP-1 molecule. These new substances are characterized by an increased stability while maintaining efficacy.

Anti-diabetogenic Action

Infusion and subcutaneous injection of GLP-1 cause a considerable increase of insulin secretion and an inhibition of glucagon release in patients with diabetes mellitus type II (Gutniak, M. (1992); Kreymann, B. (1987); Nathan, D. M. (1992); Nauck, M. A. (1993a & b)). Both are of therapeutic interest and are involved in the blood sugar lowering effect of GLP-1: insulin promotes glucose uptake by its target tissue and inhibits gluconeogenesis. Furthermore GLP-1 analogues would be expected to increase glucose uptake in the periphery. The inhibition of glucagon secretion must be regarded as an indirect GLP-1 effect since glucagon-producing A cells express no GLP-1 receptors (Komatsu, R. (1989)). On the contrary, the increased insulin and somatostatin release appear to be the decisive factor. Both hormones are known as inhibitors of glucagon release.

Two molecular mechanisms certainly contribute to the GLP-1-induced insulin release in diabetes mellitus type II. In addition to directly amplifying the glucose-induced insulin release, GLP-1 sensitizes a subgroup of B cells towards the key stimulus "glucose" (Fehmann, H. C. (1991)) and possibly also towards further stimuli so that overall more B cells secrete insulin. This prizing affect is the most likely explanation for the fact that GLP-1 leads to a prolonged release of insulin despite its relatively short plasma half-life.

This effect depends on increased glucose levels (>108 mg/dl) (Göke, R. (1993a)). It distinguishes GLP-1 fundamentally from the sulfonylureas which influence insulin secretion independently of the plasma level of glucose. If the glucose value decreases below 108 mg/dl, the insulin secretion dries up even with an intravenous infusion of GLP-1. Hence hypoglycaemias would be hardly expected when GLP-1 is used therapeutically. In fact they have also not been described in the previous clinical studies. However, the pharmacokinetic properties of GLP-1 are problematic. The duration of action is limited due to its very short half-life.

From a therapeutic point of view the synthesis of stable and strongly effective GLP-1 peptide analogues is in any case desirable. Peptide analogues have now been synthesized based on the molecule exendin that was originally isolated from the venom of lizards with the aim of developing improved therapeutic agents that are stable towards degradation with an increased duration of action for the treatment of diabetes mellitus. These peptides have the same pharmacological effect as GLP-1, but surprisingly have a considerably longer half-life.

The new peptide sequences described as the subject matter of the invention have an effect on insulin synthesis and insulin release and an action on the insulin effect especially the uptake of glucose into the target tissues, muscle and fat tissue as well as emptying of the stomach.

SUBJECT MATTER OF THE INVENTION

The present invention is based on the sequence of exendin-3 and exendin-4, peptides which were isolated from the secretory product of *Heloderma horridum* or *Heloderma suspectum* (Eng. J. et al. (1990, 1992)). The amino acid sequence and effect of the two peptides on the pancreas has already been published by several authors (Eng. J. et a. (1990); Raufman, J. P. (1992); Göke, R. (1993b); Thorens, B. (1993)). The subject matter of this invention are new truncated exendin fragments which comprise the amino acid sequences of exendin-3-(1–30) or exendin-4-(1–30) in which the C-terminal end of these sequences can be shortened by up to 3 amino acids, preferably by at most 1 amino acid, and the N-terminal end can be shortened by up to 2 and preferably at most 1 amino acid. Surprisingly these exendin fragments are biologically active although the amino acid sequence is shortened. Shortened amino acid sequences are more economical to produce than relatively longer sequences. Hence, peptide fragments with the following sequences are particularly preferred; especially peptide fragments that are based on exendin-3-(1–30) (SEQ ID NO.1):

SEQ ID NO:1 based on exendin-3

```
1         5          10          15
H S D G T F T S D L S K Q M E E E A V 20        25         30
R L F I E W L K N G X₁
```

SEQ ID NO:2 based on exendin-4

```
1         5          10          15
H G E G T F T S D L S K Q M E E E A V 20        25         30
R L F I E W L K N G X₁
``` in which the amino acids at position 1, 2, 28, 29 or 30 can be part of the sequence depending on the desired chain length. The peptides are numbered through from the N-terminus to the C-terminus. $X_1$ denotes a proteogenic or non-proteogenic amino acid apart from glycine. Exendin and exendin analogues with a chain length of 1–27 are preferred and especially those with a chain length of 1–30.

The carboxyl group $COR_3$ of the amino acid at the C-terminal end can be present in a free form ($R_3$=OH) or in the form of a physiologically tolerated alkaline or alkaline earth salt such as e.g. a sodium, potassium or calcium salt. The carboxyl group can also be esterified with primary, secondary or tertiary alcohols such as e.g. methanol, branched or unbranched $C_1$–$C_6$-alkyl alcohols, in particular ethyl alcohol or tert. butanol. The carboxyl group can, however, also be amidated with primary or secondary amines such as ammonia, branched or unbranched $C_1$–$C_6$ alkylamines or $C_1$–$C_6$ di-alkylamines, in particular methylamine or dimethylamine.

The amino group of the amino acid $NR_1R_2$ at the N-terminal end can be present in a free form ($R_1$, $R_2$=H) or in the form of a physiologically tolerated salt such as e.g. a chloride or acetate. The amino group can also be acetylated with acids so that $R_1$=H and $R_2$=acetyl, trifluoroacetyl, adamantyl or be present in a form protected by conventional amino protecting groups of peptide chemistry such as e.g. Fmoc, Z, Boc, Alloc or be N-alkylated in which $R_1$ and/or $R_2$=$C_1$–$C_6$ alkyl or $C_2$–$C_8$ alkenyl or $C_7$–$C_9$ aralkyl.

Alkyl residues are understood as straight-chained, branched or optionally ring-shaped alkyl residues, preferably methyl, ethyl, isopropyl and cyclohexyl.

All exendin fragments can be present as completely or partially protected derivatives.

A further subject matter of this invention are exendin fragments with the above-mentioned properties and sequence lengths in which at least one but at most eleven of the modifications listed under (a) to (p) have been additionally carried out. Exendin fragments are preferred which have at most nine and particularly preferably those which have at most five of the modifications listed under (a) to (p).

(a) The α-amino acid in position 1 is D-His, Ala, D-Ala, Gly, Lys or D-Lys of which Ala, Gly or Lys are particularly preferred; or
(b) the α-amino acid in position 2 is Ser, D-Ser, Thr, D-Thr, Gly, Ala, D-Ala, Ile, D-Ile, Val, D-Val, Leu or D-Leu, preferably Ser, Thr, Gly, Ala, Val, Ile or Leu; or
(c) the α-amino acid in position 3 is Glu, D-Glu, Asp, D-Asp, Ala or D-Ala, preferably Glu, Asp or Ala; or
(d) the amino acid in position 4 is Ala, D-Ala or β-Ala, preferably Ala; or
(e) the α-amino acid in position 5 is Ser, Tyr or Ala; or
(f) the α-amino acid in position 6 is Ala, Ile, Val, Leu, Cha or Tyr, preferably Ala, Ile, Val, Leu or Tyr; or
(g) the α-amino acid in position 7 is Ala, D-Ala, Tyr, D-Tyr, Ser, D-Ser or D-Thr, preferably Ala, Tyr or Ser; or
(h) the α-amino acid in position 8 is Ala, Tyr or Thr; or
(i) the α-amino acid in position 9 is Ala, D-Ala, Glu, D-Glu or D-Asp, preferably Ala or Glu; or
(j) the amino acids in position 10, 11, 12, 15, 16, 17, 18, 19, 20, 21, 24, 28, 29 are independently of one another a proteinogenic or non-proteinogenic D- or L-amino acid, preferably a proteinogenic L-amino acid; or
(k) the α-amino acid in position 13 is a neutral L-amino acid, preferably a neutral proteinogenic L-amino acid; or
(l) the α-amino acid in position 14 is, for the purposes of stabilization, replaced by a neutral L- or D-amino acid, apart from L-leucine, preferably by Nle, D-Nle, Ala, D-Ala, Ile, D-Ile, Val or D-Val, wherein Ile, Val or Ala are particularly preferred; or
(m) the α-amino acid in position 22 is D-Phe, Tyr, D-Tyr, Leu, D-Leu, Val, D-Val, L-Cha, D-Cha, β-1-Nal, β-2-Nal or β-1-D-Nal, wherein Tyr, Leu or Val are preferred; or
(n) the α-amino acid in position 23 is Leu, D-Leu, D-Ile, Val, D-Val, L-Cha, D-Cha, Tyr, D-Tyr, Phe or D-Phe, wherein Leu, Val, Tyr or Phe are preferred; or
(o) the α-amino acid in position 25, 26 or 27 is a neutral L- or D-amino acid, preferably a neutral, proteinogenic L-amino acid; or
(p) the α-amino acid in position 30 is a proteinogenic or non-proteinogenic D- or L-amino acid apart from glycine, preferably Arg, D-Arg, Tyr or D-Tyr, Arg or Tyr are particularly preferred.

Among the new exendin fragments, those are particularly preferred which contain the amino acid leucine at position 10 and/or the amino acid valine at position 19, the amino acid isoleucine or alanine instead of methionine at position 14 and arginine at position 30 in addition to the already mentioned properties and sequence lengths. Those modifications of exendin fragments are also particularly preferred in which, in addition to the particularly preferred amino acids at positions 10, 14, 19 and 30, one of the 20 known proteinogenic L-amino acids is located at position 2.

Preferred exendin analogues have a substitution at position 3 or 14, particularly preferably at position 2 and especially preferably the exendin analogues only contain proteinogenic amino acids.

In addition to new shortened and stabilized exendin-3 and exendin-4 analogues, the invention also concerns processes for producing these analogues in which the analogues are prepared in a solid phase synthesis from protected amino acids contained in the analogues which are coupled in sequence and correspond to the amino acids in the analogues and which are optionally supplemented with corresponding amino acids which do not occur in the natural exendin peptides.

The glycine at position 30 of the exendin-3 or exendin-4 sequence was substituted by another proteogenic or non-proteogenic amino acid in order to avoid diketopiperazine formation during the synthesis after cleavage of the amino terminal protective group.

The exendin-(1–30) analogues and fragments are advantageous compared to the exendins-1-(1–39) since the shorter sequences of these analogues enable a more simple synthesis in higher yields.

The abbreviations and definitions of the amino acids that are used were recommended in Pure Appl. Chem. 31, 639–45 (1972) and ibid. 40, 277–90 (1974) and correspond to the PCT rules (WIPO standard st. 23:Recommendation for the Presentation of Nucleotide and Amino Acid Sequences in Patent Applications and in Published Patent Documents). The one and three letter codes are as follows:

| Amino acid abbreviations | | |
|---|---|---|
| Amino acid | three letter code | one letter code |
| alanine | Ala | A |
| arginine | Arg | R |
| asparagine | Asn | N |
| aspartic acid | Asp | D |
| cysteine | Cys | C |
| glutamine | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |

-continued

Amino acid abbreviations

| Amino acid | three letter code | one letter code |
|---|---|---|
| tyrosine | Tyr | Y |
| valine | Val | V |
| other amino acids | Xaa | X |

The abbreviations represent L-amino acids if not specified otherwise such as D- or D,L-. The D-amino acids are written in small letters in the one letter code. Certain natural as well as non-natural amino acids are achiral e.g. glycine. In the representation the N-terminal end of all peptides is on the left and the C-terminal end is on the right.

Examples of non-proteinogenic amino acids are given in the following list together with their abbreviations:

| | |
|---|---|
| β-alanine | β-Ala |
| o-aminobenzoic acid | Oab |
| m-aminobenzoic acid | Mab |
| p-aminobenzoic acid | Pab |
| m-aminomethylbenzoic acid | Amb |
| ω-aminohexanoic acid | Ahx |
| ω-aminoheptanoic acid | Ahp |
| ω-aminooctanoic acid | Aoc |
| ω-aminodecanoic acid | Ade |
| ω-aminotetradecanoic acid | Atd |
| citrulline | Cit |
| cyclohexylalanine | Cha |
| α,γ-diaminobutyric acid | Dab |
| α,β-diaminopropionic acid | Dap |
| methionine sulfoxide | Met(O) |
| c$^\alpha$-methyl-alanine | Aib |
| N-methyl-glycine (sarcosine) | Sar |
| naphthylalanine | Nal |
| norleucine | Nle |
| ornithine | Orn |
| 1,2,3,4-tetrahydroisoquinoline-3-carboxylic acid | Tic |

All amino acids can be divided into the following three main classes according to their physical-chemical properties:

Acidic: The amino acid releases a proton in aqueous solution and at physiological pH and consequently carries a negative charge.

Basic: The amino acid accepts a proton in aqueous solution and at physiological pH and consequently carries a positive charge.

Neutral: The amino acid is in an uncharged state in aqueous solution and at physiological pH.

The definition "carries a positive/negative charge" or "is in an uncharged state" only applies when on statistical average a significant number of a class of amino acids (at least 25%) are in the state.

In addition to the 20 so-called proteinogenic amino acids whose incorporation into proteins is controlled by the information of the genetic code, non-proteinogenic amino acids can also be incorporated into peptide sequences by the described synthesis process. A list of the proteinogenic amino acids and their classification into the above-mentioned three classes is given in Table 1. Non-proteinogenic amino acids are not genetically coded. Examples of non-proteinogenic amino acids and their classification into acidic, basic or neutral amino acids is given in Table 1.

TABLE 1

| | proteinogenic | non-proteinogenic |
|---|---|---|
| acidic | Asp, Glu | |
| basic | Arg, His, Lys | Dab, Dap, Orn |
| neutral | Ala, Asn, Cys, Gln, Gly, Ile, Leu, Met, Phe, Pro, Ser, Thr, Trp, Tyr, Val | β-Ala, Aib, Cit, Cha, Oab, Mab, Pab, Amb, Ahx, Ahp, Aoc, Ade, Atd, Nal, Nle, Sar, Tic |

The exendin analogoues which are a subject matter of the invention have advantageous therapeutic properties. Hence they lead to a stimulation of insulin release from the endocrine pancreas, to an increase of insulin biosynthesis and to increased peripheral glucose utilization. Since these effects can only be observed when the blood sugar levels are at the same time increased, a hypoglycemia would not be expected to occur after their administration. Furthermore the exendin analogues inhibit glucagon release from the endocrine pancreas and lead to a decrease of gluconeogenesis. In non-insulin dependent diabetes mellitus (NIDDM) the exendin analogues result in a considerable improvement of the metabolic situation. In particular the glucose uptake in muscle and fat tissue is increased independently of the insulin secretory effect. Due to the inhibitory effect on glucagon release, it is also appropriate to administer the exendin analogues in insulin dependent diabetes mellitus. Compared to glucagon-like peptide 1 (GLP-1) and the known exendin-3 and exendin-4 sequences, the exendin analogues according to the invention surprisingly have a higher efficacy in the various test systems so that they are more suitable for a therapeutic application than GLP-1, exendin-3 or exendin-4. The advantages of the new exendin analogues are in particular as follows: higher stability towards degradation and metabolism, longer duration of action, effectiveness at lower doses. Analogues based on exendin-3 are particularly preferred which exhibit particularly long durations of action or effectiveness at particularly low doses.

Solid phase and liquid phase synthesis is a conventional process for synthesizing peptides. In order to optimize the process for the synthesis of a particular product with regard to the purity of the crude product and yield, it is necessary that the process parameters and the materials that are used, for example the support material, the reagents which should make groups react, the materials for blocking the groups which should not react or the reagents which cleave blocking materials are adapted to the product to be synthesized, to the intermediate products to be synthesized and the starting materials. This adaptation is not simple with regard to the interdependency of the many process parameters.

Pharmaceutical preparations which contain the peptides according to the invention individually or together as an active substance in addition to conventional auxiliary substances and additives are preferably administered parenterally (subcutaneously, intramuscularly or intravenously). However, all other common forms of administration such as oral, rectal, buccal (including sublingual), pulmonary, transdermal, iontophoratic, vaginal and intranasal administration come into consideration. The drug has an insulin-regulating effect thereby promoting in an advantageous manner the compensation of the blood sugar level. It is advantageous for the use of the drug when blood levels between 20 and 50 pmol/l are attained. Infusion rates of 0.4–1.2 pmol/kg/min are necessary for this. In the case of a subcutaneous or buccal administration, substance quantities of 5–500 nmol are necessary depending on the galenic form and intended duration of action.

The exendin analogues according to the invention or pharmacologically acceptable salts thereof are preferably stored as sterile lyophilisates and mixed with a suitable isotonic solution before administration. The analogues can then be injected, infused or optionally also absorbed through the mucous membranes in this form. The conventional isotonic aqueous systems that are suitable for injection or infusion which contain common additives for injection solutions such as stabilizers and solubilizers can be used as solvents. Physiological saline solution or optionally solutions made isotonic by buffers are preferred in this case.

Additives are, for example, tartrate or citrate buffer, ethanol, complexing agents (such as ethylene diamintetraacetic acid and non-toxic salts thereof), high molecular polymers (such as liquid polyethylene oxide) to regulate the viscosity. Liquid carrier substances for injection solutions must be sterile and are preferably filled into ampoules. Solid carrier substances are for example starch, lactose, mannitol, methyl cellulose, talcum, highly dispersed silicic acids, higher molecular weight fatty acids (such as stearic acid), gelatin, agar-agar, calcium phosphate, magnesium stearate, animal or vegetable fats, solid high molecular polymers (such as polyethylene glycol); suitable preparations for oral administration can if desired contain flavourings or sweeteners. For nasal administration surfactants can be added to improve absorption through the nasal mucous membrane e.g. cholic acid, taurocholic acid, chenodeoxycholic acid, glycolic acid, dehydrocholic acid, deoxycholic acid and cyclodextrins.

The daily dose to be administered is in a range of 150–500 nmol. The determination of the biological activity is based on measurements compared to international reference preparations for glucagon-like peptide-1, exendin-3 or exendin-4 in a conventional test procedure for glucagon-like peptide-1.

The exendin analogues according to the invention can be prepared by conventional processes in peptide synthesis as described for example in J. M. Steward and J. D. Young "Solid Phase Peptide Synthesis", 2nd ed., Pierce Chemical Co., Rockford, Ill. (1984) and in J. Meienhofer Hormonal Proteins and Peptides, Vol.2 Academic Press, New York (1973) for solid phase synthesis and in E. Schroder and K. Lubke "The Peptides", Vol.1, Academic Press, New York (1965) for liquid phase synthesis.

General Processes for Peptide Synthesis

In general protected amino acids are added to a growing peptide chain for the synthesis of peptides. Either the amino group or the carboxyl group as well as any reactive group in the side chain of the first amino acid are protected. This protected amino acid is either coupled to an inert support or it can also be used in solution. The next amino acid in the peptide sequence is appropriately protected under conditions which favour the formation of an amide bond and is added to the first. After all desired amino acids have been coupled in the correct sequence, the protective groups and optionally the support phase are cleaved. The crude polypeptide that is obtained is reprecipitated and preferably purified chromatographically to form the final product.

A preferred method for synthesizing analogues of physiologically active polypeptides with fever than fourty amino acids comprises a solid phase peptide synthesis. In this method the α-amino functions ($N^\alpha$) and any reactive side chains are protected with acid-labile or base-labile groups. The protective groups that are used should be stable under the conditions for linking amide bonds but it should be possible to readily cleave them without impairing the polypeptide chain that has formed. Suitable protective groups for the α-amino function include the following groups but are not limited to these: t-butyloxycarbonyl (Boc), benzyloxycarbonyl (Z), o-chlorbenzyloxycarbonyl, bi-phenylisopropyloxycarbonyl, tert.-amyloxycarbonyl (Amoc), α,α-dimethyl-3,5-dimethoxy-benzyloxycarbonyl, o-nitrosulfenyl, 2-cyano-t-butoxy-carbonyl, 9-fluorenylmethoxycarbonyl (Fmoc), 1-(4,4-dimethyl-2,6-dioxocylohex-1-ylidene)ethyl (Dde) and the like. 9-Fluorenylmethoxycarbonyl (Fmoc) is preferably used as the $N^\alpha$-protective group.

Suitable side chain protective groups include the following but are not limited to these: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl (2-ClZ), 2,6-dichlorobenzyl, cyclohexyl, cyclopentyl, 1-(4,4-dimethyl-2,6-dioxocyclohex-1-ylidene) ethyl (Dde), isopropyl, 4-methoxy-2,3–6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis the C-terminal amino acid is coupled as the first to a suitable support material. Suitable support materials are those which are inert towards the reagents and reaction conditions for the stepwise condensation and cleavage reactions and which do not dissolve in the reaction media that are used. Examples of commercially available support materials include styrene/divinylbenzene copolymers which have been modified with reactive groups and/or polyethylene glycol and also chloromethylated styrene/divinylbenzene copolymers, hydroxymethylated or aminomethylated styrene/divinylbenzene copolymers and the like. Polystyrene (1%)-divinylbenzene or TentaGel® (Rapp Polymere, Tübingen) derivatized with 4-benzyloxybenzyl-alcohol (Wang-anchor (Wang, S. S. 1973)) or 2-chlorotrityl chloride (Barlos, K. et al. 1989) is preferably used if it is intended to prepare the peptidic acid. In the case of the peptide amide, polystyrene (1%) divinylbenzene or TentaGel® derivatized with 5-(4'-aminomethyl)-3',5'-dimethoxyphenoxy)valeric acid (PAL-anchor) (Albericio, F. et al. 1987) or p-(2,4-dimethoxyphenyl-amino methyl)-phenoxy group (Rink-Amid anchor (Rink, H. 1987)) is preferred.

The linkage to the polymeric support can be achieved by reacting the C-terminal Fmoc-protected amino acid with the support material with the addition of an activation reagent in ethanol, acetonitrile, N,N-dimethylformamide (DMF), dichloromethane, tetrahydrofuran, N-methylpyrrolidone or similar solvents preferably in DMF at room temperature or elevated temperatures e.g. between 40° C. and 60° C., preferably at room temperature and with reaction times of 2 to 72 hours, preferably about 2×2 hours.

The coupling of the $N^\alpha$ protected amino acid preferably the Fmoc amino acid to the PAL, Wang or Rink anchor can for example be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, o-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or also in the absence of 1-hydroxybenzotriazole or 1-hydroxy-7-azabenzotriazole preferably with the aid of TBTU with addition of HOBt, with or without the addition of a base such as for example diisopropylethylamine (DIEA), triethylamine or N-methylmorpholine, preferably diisopropylethylamine with reaction times of 2 to 72 hours, preferably 3 hours in a 1.5 to 3-fold excess of the amino acid and the coupling reagents, preferably in a 2-fold excess and at temperatures between about 10° C. and 50° C., preferably 25° C. in a solvent such as dimethylformamide, N-methylpyrrolidone or dichloromethane, preferably dimethylformamide. Instead of the coupling reagents it is also possible to use the active esters (e.g. pentafluorophenyl, p-nitrophenyl or the like), the symmetric anhydride of the $N^\alpha$-Fmoc-amino acid, its acid chloride or acid fluoride under the conditions described above.

The $N^\alpha$-protected amino acid, preferably the Fmoc amino acid is preferably coupled to the 2-chlorotrityl resin in dichloromethane with the addition of DIEA with reaction times of 10 to 120 minutes, preferably 20 minutes but is not limited to the use of this solvent and this base.

The successive coupling of the protected amino acids can be carried out according to conventional methods in peptide synthesis typically in an automated peptide synthesizer. After cleavage of the $N^\alpha$-Fmoc protective group of the coupled amino acid on the solid phase by treatment with piperidine (10% to 50%) in dimethylformamide for 5 to 20 minutes, preferably 2×2 minutes with 50% piperidine in DMF and 1×15 minutes with 20% piperidine in DMF, the next protected amino acid in a 3 to 10-fold excess, preferably in a 10-fold excess is coupled to the previous amino acid in an inert, non-aqueous, polar solvent such as dichloromethane, DMF or mixtures of the two, preferably DMF and at temperatures between about 10° C. and 50° C., preferably at 25° C. The reagents that have already been mentioned for coupling the first $N^\alpha$-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis the peptide is cleaved from the support material while simultaneously cleaving the side chain protecting groups. Cleavage can be carried out with trifluoroacetic acid or other strongly acidic media with addition of 5%–20% V/V scavengers such as dimethylsulfide, ethylmethylsulfide, thioanisole, thiocresol, m-cresol, anisole ethanedithiol, phenol or water, preferably 15% v/v dimethylsulfide/ethanedithiol/m-cresol 1:1:1 within 0.5 to 3 hours, preferably 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about –10° C. and 50° C., preferably about 25° C. and reaction times between about 12 and 24 hours, preferably about 18 hours. In addition the peptide can also be cleaved from the support by re-esterification e.g. with methanol.

The acidic solution that is obtained is admixed with a 3 to 20-fold amount of cold ether or n-hexane, preferably a 10-fold excess of diethyl ether, in order to precipitate the peptide and hence to separate the scavengers and cleaved protective groups that remain in the ether. A further purification can be carried out by re-procipitating the peptide several times from glacial acetic acid. The precipitate that is obtained is taken up in water or tert. butanol or mixtures of the two solvents, preferably a 1:1 mixture of tert, -butanol/water and freeze-dried.

The peptide obtained can be purified by some or all of the following chromatographic methods: ion exchange over a weakly basic resin in the acetate form; hydrophobic adsorption chromatography on non-derivatized polystyrene/divinylbenzene copolymers (e.g. Amberlite® XAD); adsorption chromatography on silica gel; ion exchange chromatography e.g. on carboxymethyl cellulose; distribution chromatography e.g. on Sephadex® G-25; countercurrent distribution chromatography; or high pressure liquid chromatography (HPLC) in particular reversed-phase HPLC on octyl or octadecylsilylsilica (ODS) phases.

In summary part of the present invention encompasses processes for the preparation of polypeptides and pharmaceutically usable salts thereof. These processes which lead to physiologically active shortened homologues and analogues of exendin-3 or exendin-4 with the above-mentioned preferred chain lengths and modifications comprise processes for the sequential condensation of protected amino acids on a suitable support material, methods for cleaving the support and protective groups and for purifying the crude peptides that are obtained.

The amino acid analysis Was carried out with an amino acid analyzer 420 A from the Applied Biosystems Company (Weiterstadt). 50 to 1000 pmol of the sample to be analysed was applied to the sample carrier in 10 to 40 $\mu$l solution and subsequently fully automatically hydrolysed for 90 minutes in the gas phase at 160° C. with 6 N hydrochloric acid, derivatized with phenylisothiocyanate and analysed on-line by a microbore HPLC. Mass spectroscopic examinations were carried out on an API III triple-quadrupole mass spectrometer (SCIEX; Thornhill, Canada) equipped with an ion spray ion source.

The protected amino acid derivatives can for example be obtained from Novabiochem GmbH (Bad Soden).

The following examples only represent an illustrative selection of the inventive thought and not a limitation of the subject matter of the invention.

EXAMPLE 1

HGEGTFTSDLSKQ-Nle-EEEAVRLFIEWLKNGR-NH$_2$ (SEQ ID NO.3) [Nle$^{14}$, Arg$^{30}$]-exendin-4-(1–30)-NH$_2$ Example 1 was synthesized in a 0.02 mmol batch by the solid phase method on 5-(4'-aminomethyl)-3 ',5'-dimethoxyphenoxy)valerianyl-alanyl-aminomethyl-polystyrene(1%)divinylbenzene (loading: 0.5 mmol/g) on a multiple automated peptide synthesizer SyRo II from the MultiSyn Tech Company (Bochum). The α-amino functional groups of the amino acids were protected with 9-fluorenylmethoxycarbonyl (Fmoc). The side chain protective groups were t-butyl (tBu) for Asp, Glu, Ser and Thr, trityl (Trt) for Asn, Gln and His, t-butyloxycarbonyl (Boc) for Lys and Trp and 2,2,5,7,8-pentaethylchroman-6-sulfonyl (Pmc) for Arg. The protected amino acids were coupled sequentially in a 10-fold excess using double couplings of 2 times 40 minutes duration and using N,N-diisopropylcarbodiimide/1-hydroxybenzo-triazole as activation reagents. The peptide was cleaved from the polymeric support while simultaneously cleaving the protective groups in trifluoroacetic acid (85%) in the presence of 15% ethanedithiol/dimethylsulfide/m-cresol (1:1:1 v/v/v) for 120 minutes at room temperature. Subsequently the peptide was precipitated with anhydrous diethyl ether and then washed several times with anhydrous diethyl ether to completely remove the thiols. Freeze-drying of the precipitate from water/tert. butanol (1:1) yielded 62 mg of the crude peptide. The crude peptide was purified within 30 minutes by reversed-phase HPLC with a gradient of 37% to 42% acetonitrile/0.9% TFA. The eluate was evaporated, lyophilized and gave a yield of 29 mg of a white solid with a purity of ≧97%.

Amino acid analysis; Ala 1,08 (1); Asx 1,91 (2); Glx 6,10 (6); Phe 1,78 (2); Gly 3,10 (3); His 1,00 (1); Ile 0,88 (1); Lys 2,02 (2); Leu 3,24 (3); Nle 1,10 (1); Arg 1,98 (2); Ser 2,04 (2); Thr 1,99 (2); Val 0,91 (1); Trp 0,87 (1)

ESI-MS: 3488.2

EXAMPLE 2

HGEGTFTSDLSKQ-Nle-EEEAVRLFIEWLKNGY-NH$_2$ (SEQ ID No. 4) [Nle$^{14}$, Tyr$^{30}$]-exendin-4-(1–30)-NH$_2$ Example 2 was synthesized in a 0.0076 mmol batch by the solid phase method on TentaGel® (Rapp Polymers, Tübingen) which was derivatized with a Rink-amide anchor (4-(2',4'-dimethoxyphenyl-aminomethyl)-phenoxy group) (loading: 0.18 mmol/g) on a multiple automated peptide synthesizer SyRo II from the MultiSynTech Company (Bochum). The protected amino acids that were used were analogous to example 1, The protected amino acids were sequentially coupled in an eight-fold excess with single couplings of 40 minutes duration at 40° C. and while stirring. 2-(1H-benzotriazol-1-yl)-1,1,3,3-tetramethyluronium tetrafluoroborate (TBTU)/1-hydroxybenzotriazole were used as activation reagents with the addition of diisopropylethylamine. The peptide was cleaved and purified analogously to example 1. 18.1 mg of a while solid with a purity of >95% was obtained.

Amino acid analysis: Ala 1,03 (1); Asx 1,90 (2); Glx 6,24 (6); Phe 1,94 (2); Gly 3,12 (3); His 1,02 (1); Ile 1,09 (1); Lys 2,01 (2); Leu 3,06 (3); Nle 1,08 (1); Arg 0,97 (1); Ser 1,98 (2); Thr 1,80 (2); Val 0,93 (1); Trp 1,01 (1); Tyr 0,90 (1).

ESI-MS: 3494.8

EXAMPLE 3

HSDGTFTSDLSKQ-Nle-EEEAVRLFIEWLENGR-H$_2$ (SEQ ID No. 5) [Nle$^{14}$, Arg$^{30}$]-exendin-3-(1–30)-NH$_2$ Example 3 was synthesized analogously to the method described for example 2. 17.6 mg of a white solid with a purity of ≧99% was obtained.

Amino acid analysis: Ala 0,99 (1); Asx 2,98 (3); Glx 5,16 (5); Phe 2,08 (2); Gly 2,16 (2); His 0,95 (1); Ile 1,03 (1); Lys 2,04 (2); Leu 2,91 (3); Nle 1,05 (1); Arg 1,04 (1); Ser 3,00 (3); Thr 2,05 (2); Val 1,01 (1); Trp 1,18 (1); Tyr 0,98 (1).

ESI-MS: 3504,4

EXAMPLE 4

HGEGTFTSDLSKQMEEEAVRLFIEWLKNGR-NH$_2$ (SEQ ID No. 6) [Arg$^{30}$]-exendin-4-(1–30)-NH$_2$ Example 4 was synthesized analogously to the method described for example 1. 17.9 mg of a white solid with a purity of ≧96% was obtained.

Amino acid analysis: Ala 0,96 (1); Asx 2,01 (2); Glx 6,00 (6); Phe 1,80 (2); Gly 3,21 (3); His 0,96 (1); Ile 1,07 (1); Lys 1,92 (2); Leu 2,98 (3); Met 1,06 (1); Arg 1,90 (2); Ser 1,91 (2); Thr 2,09 (2); Val 0,97 (1); Trp 0,84 (1).

ESI-MS: 3508,4

EXAMPLE 5

GEGTFTSDLSKQ-Nle-EEEAVRLFIEWLKNGR-NH$_2$ (SEQ ID No. 7) [Nle$^{14}$, Arg$^{30}$]-exendin-4-(2–30)-NH$_2$ Example 5 was synthesized analogously to the method described for example 2. 13.2 mg of a white solid with a purity of ≧97% was obtained.

Amino acid analysis: Ala 1,04 (1); Asx 1,98 (2); Glx 6,08 (6); Phe 1,86 (2); Gly 2,91 (3); Ile 0,96 (1); Lys 1,84 (2); Leu 2,98 (3); Nle 1,04 (1); Arg 1,90 (2); Ser 1,94 (2); Thr 1,92 (2); Val 0,96 (1); Trp 0,85 (1).

ESI-MS: 3350,8

EXAMPLE 6

HGEGTFTSDLSKQMEEEAVRAFIEWLKNGR-NH$_2$ (SEQ ID No. 8) [Ala$^{21}$, Arg$^{30}$]-exendin-4-(1–30)-NH$_2$ Example 6 was synthesized analogously to the method described for example 1. 11.1 mg of a white solid with a purity of ≧95% was obtained.

Amino acid analysis: Ala 2,08 (2); Asx 1,93 (2); Glx 6,07 (6); Phe 1,74 (2); Gly 2,97 (3); His 0,98 (1); Ile 0,87 (1); Lys 2,15 (2); Leu 2,02 (2); Met 0,96 (1); Arg 2,13 (2); Ser 1,87 (2); Thr 2,07 (2); Val 1,04 (1); Trp 0,87 (1).

ESI-MS: 3466,3

EXAMPLE 7

HGEGTFTSDLSKQMEEEAVRLFIEWLKAGR-NH$_2$ (SEQ ID No. 9) [Ala$^{28}$, Arg$^{30}$]-exendin-4-(1–30)-NH$_2$ Example 7 was synthesized analogously to the method described for example 1. 15.0 mg of a white solid with a purity of ≧97% was obtained.

Amino acid analysis: Ala 1,98 (2); Asx 0,98 (1); Glx 6,22 (6); Phe 1,92 (2); Gly 3,03 (3); His 0,99 (1); Ile 1,03 (1); Lys 2,05 (2); Leu 3,03 (3); Met 0,96 (1); Arg 1,84 (2); Ser 1,98 (2); Thr 2,09 (2); Val 1,01 (1); Trp 0,72 (1).

ESI-MS: 3465,4

EXAMPLE 8

HGEGTFTSDLSKQMEEEAVRAFIEWLKAGR-NH$_2$ (SEQ ID No. 10) [Ala$^{21,28}$, Arg$^{30}$]-exendin-4-(1–30)-NH$_2$ Example 8 was synthesized analogously to the method described for example 1. 18.4 mg of a white solid with a purity of ≧95% was obtained.

Amino acid analysis: Ala 3,12 (3); Asx 0,99 (1); Glx 6,04 (6); Phe 1,80 (2); Gly 3,00 (3): His 0,96 (1); Ile 1,02 (1); Lys 1,84 (2); Leu 1,97 (2); Met 0,98 (1); Arg 2,03 (2); Ser 1,91 (2); Thr 1,88 (2); Val 0,99 (1); Trp 0,99 (1).

ESI-MS: 3423,3

EXAMPLE 9

It was possible to prepare the following exendin derivatives in high purity in an analogous manner. (Ex-4=exendin-4, Ex-3=exendin-3)

| Exendin-Derivative | Seq. | Sequence |
|---|---|---|
| [A$^{14}$, R$^{30}$]-Ex-4-(1-30)—OH | 11 | HGEGTFTSDLSKQAEEEAVRLFIEWLKNGR—OH |
| Ac-[Ile$^{14}$, R$^{30}$]-Ex-4-(1-30)—NH$_2$ | 12 | Ac-HGEGTFTSDLSKQIleEEEAVRLFIEWLKNGR—NH$_2$ |
| [Nle$^{14}$]-Ex-4-(1-27)—NH$_2$ | 13 | HGEGTFTSDLSKQNleEEEAVRLFIEWLK—NH$_2$ |
| [A$^{14,29}$, R$^{30}$]-Ex-3-(1-30)—NH$_2$ | 14 | HSDGTFTSDLSKQAEEEAVRLFIEWLKNAR—NH$_2$ |
| [A$^{14,27}$, R$^{30}$]-Ex-3-(1-30)—NH$_2$ | 15 | HSDGTFTSDLSKQAEEEAVRLFIEWLANGR—NH$_2$ |
| [A$^{14,26}$, R$^{30}$]-Ex-3-(1-30)—NH$_2$ | 16 | HSDGTFTSDLSKQAEEEAVRLFIEWAKNGR—NH$_2$ |
| [A$^2$, Nle$^{14}$, R$^{30}$]-Ex-4-(1-30)—NH$_2$ | 17 | HAEGTFTSDLSKQNleEEEAVRLPIEWLKNGR—NH$_2$ |
| [C$^2$, Nle$^{14}$, R$^{30}$]-Ex-4-(1-30)—NH$_2$ | 18 | HCEGTFTSDLSKQNleEEEAVRLFIEWLKNGR—NH$_2$ |
| [D$^2$, Nle$^{14}$, R$^{30}$]-Ex-4-(1-30)—NH$_2$ | 19 | HDEGTFTSDLSKQNleEEEAVRLFIEWLKNGR—NH$_2$ |
| [E$^2$, Nle$^{14}$, R$^{30}$]-Ex-4-(1-30)—NH$_2$ | 20 | HEEGTFTSDLSKQNleEEEAVRLFIEWLKNGR—NH$_2$ |
| [F$^2$, Nle$^{14}$, R$^{30}$]-Ex-4-(1-30)—NH$_2$ | 21 | HPEGTFTSDLSKQNleEEEAVRLFIEWLKNGR—NH$_2$ |
| [H$^2$, Nle$^{14}$, R$^{30}$]-Ex-4-(1-30)—NH$_2$ | 22 | HHEGTFTSDLSKQNleEEEAVRLFIEWLKNGR—NH$_2$ |
| [I$^2$, Nle$^{14}$, R$^{30}$]-Ex-4-(1-30)—NH$_2$ | 23 | HIEGTFTSDLSKQNleEEEAVRLFIEWLKNGR—NH$_2$ |
| [K$^2$, Nle$^{14}$, R$^{30}$]-Ex-4-(1-30)—NH$_2$ | 24 | HKEGTFTSDLSKQNleEEEAVRLFIEWLKNGR—NH$_2$ |
| [L$^2$, Nle$^{14}$, R$^{30}$]-Ex-4-(1-30)—NH$_2$ | 25 | HLEGTFTSDLSKQNleEEEAVRLFIEWLKNGR—NH$_2$ |
| [M$^2$, Nle$^{14}$, R$^{30}$]-Ex-4-(1-30)—NH$_2$ | 26 | HMEGTFTSDLSKQNleEEEAVRLFIEWLKNGR—NH$_2$ |
| [N$^2$, Nle$^{14}$, R$^{30}$]-Ex-4-(1-30)—NH$_2$ | 27 | HNEGTFTSDLSKQNleEEEAVRLFIEWLKNGR—NH$_2$ |
| [P$^2$, Nle$^{14}$, R$^{30}$]-Ex-4-(1-30)—NH$_2$ | 28 | HPEGTFTSDLSKQNleEEEAVRLFIEWLKNGR—NH$_2$ |
| [Q$^2$, Nle$^{14}$, R$^{30}$]-Ex-4-(1-30)—NH$_2$ | 29 | HQEGTFTSDLSKQNleEEEAVRLFIEWLKNGR—NH$_2$ |
| [R$^2$, Nle$^{14}$, R$^{30}$]-Ex-4-(1-30)—NH$_2$ | 30 | HREGTFTSDLSKQNleEEEAVRLFIEWLKNGR—NH$_2$ |
| [S$^2$, Nle$^{14}$, R$^{30}$]-Ex-4-(1-30)—NH$_2$ | 31 | HSEGTFTSDLSKQNleEEEAVRLFIEWLKNGR—NH$_2$ |
| [T$^2$, Nle$^{14}$, R$^{30}$]-Ex-4-(1-30)—NH$_2$ | 32 | HTEGTFTSDLSKQNleEEEAVRLFIEWLKNGR—NH$_2$ |
| [V$^2$, Nle$^{14}$, R$^{30}$]-Ex-4-(1-30)—NH$_2$ | 33 | HVEGTFTSDLSKQNleEEEAVRLFIEWLKNGR—NH$_2$ |
| [W$^2$, Nle$^{14}$, R$^{30}$]-Ex-4-(1-30)—NH$_2$ | 34 | HWEGTFTSDLSKQNleEEEAVRLFIEWLKNGR—NH$_2$ |
| [Y$^2$, Nle$^{14}$, R$^{30}$]-Ex-4-(1-30)—NH$_2$ | 35 | HYEGTFTSDLSKQNleEEEAVRLFIEWLKNGR—NH$_2$ |
| [A$^{2,24}$, G$^{16}$, E$^{21}$, K$^{20,28}$, Q$^{17}$, R$^{30}$, S$^{12}$, V$^{27}$, Y$^{13}$]-Ex-3-(1-30)—NH$_2$ | 36 | HADGTFTSDLSSYMEGQAVKEFIAWLVKGR—NH$_2$ |
| [A$^{14,25}$, R$^{30}$]-Ex-3-(1-30)—NH$_2$ | 37 | HSDGTFTSDLSKQAEEEAVRLFIEALKNGR—NH$_2$ |
| [E$^3$, A$^{14}$, R$^{30}$]-Ex-3-(1-30)—NH$_2$ | 38 | HSEGTFTSDLSKQAEEEAVRLFIEWLKNGR—NH$_2$ |
| [A$^1$, V$^{14}$, R$^{30}$]-Ex-3-(1-30)—NH$_2$ | 39 | ASDGTFTSDLSKQVEEEAVRLFIEWLKNGR—NH$_2$ |
| [A$^{3,14}$, R$^{30}$]-Ex-4-(1-30)—NH$_2$ | 40 | HGAGTFTSDLSKQAEEEAVRLFIEWLWNGR—NH$_2$ |
| [A$^{5,14}$, R$^{30}$]-Ex-4-(1-30)—NH$_2$ | 41 | HGEGAFTSDLSKQAEEEAVRLFIEWLKNGR—NH$_2$ |
| [A$^{14}$, R$^{30}$, Y$^5$]-Ex-4-(1-30)—NH$_2$ | 42 | HGEGYFTSDLSKQAEEEAVRLFIEWLKNGR—NH$_2$ |
| [A$^{14}$, R$^{30}$, Y$^6$]-Ex-4-(1-30)—NH$_2$ | 43 | HGEGTYTSDLSKQAEEEAVRLFIEWLKNGR—NH$_2$ |
| [A$^{14}$, I$^6$, R$^{30}$]-Ex-4-(1-30)—NH$_2$ | 44 | HGEGTITSDLSKQAEEEAVRLFIEWLKNGR—NH$_2$ |
| [A$^{14}$, R$^{30}$, S$^7$]-Ex-4-(1-30)—NH$_2$ | 45 | HGEGTFSSDLSKQAEEEAVRLFIEWLKNGR—NH$_2$ |
| [A$^{14}$, R$^{30}$, Y$^7$]-Ex-4-(1-30)—NH$_2$ | 46 | HGEGTFYSDLSKQAEEEAVRLFIEWLKNGR—NH$_2$ |
| [A$^{14}$, R$^{30}$, T$^8$]-Ex-4-(1-30)—NH$_2$ | 47 | HGEGTFTTDLSKQAEEEAVRLPIEWLKNGR—NH$_2$ |
| [A$^{14}$, R$^{30}$, Y$^8$]-Ex-4-(1-30)—NH$_2$ | 48 | HGEGTFTYDLSKQAEEEAVRLFIEWLKNGR—NH$_2$ |
| [A$^{14}$, E$^9$, R$^{30}$]-Ex-4-(1-30)—NH$_2$ | 49 | HGEGTFTSELSKQAEEEAVRLFIEWLKNGR—NH$_2$ |
| [A$^{10,14}$, R$^{30}$]-Ex-4-(1-30)—NH$_2$ | 50 | HGEGTFTSDASKQAEEEAVRLFIEWLKNGR—NH$_2$ |
| [A$^{11,14}$, R$^{30}$]-Ex-4-(1-30)—NH$_2$ | 51 | HGEGTFTSDLAKQAEEEAVRLFIEWLKNGR—NH$_2$ |
| [A$^{12,14}$, R$^{30}$]-Ex-4-(1-30)—NH$_2$ | 52 | HGEGTFTSDLSAQAEEEAVRLFIEWLKNGR—NH$_2$ |
| [A$^{13,14}$, R$^{30}$]-Ex-4-(1-30)—NH$_2$ | 53 | HGEGTFTSDLSKAAEEEAVRLFIEWLKNGR—NH$_2$ |
| [A$^{14,15}$, R$^{30}$]-Ex-4-(1-30)—NH$_2$ | 54 | HGEGTFTSDLSKQAAEEAVRLFIEWLKNGR—NH$_2$ |
| [A$^{14,16}$, G$^1$, R$^{30}$, S$^5$]-Ex-3-(1-30)—NH$_2$ | 55 | GSDGSFTSDLSKQAEAEAVRLFIEWLWNGR—NH$_2$ |
| [A$^{14,17}$, K$^1$, R$^{30}$]-Ex-4-(1-30)—NH$_2$ | 56 | KGEGTFTSDLSKQAEEEAVRLFIEWLKNGR—NH$_2$ |
| [A$^{14}$, L$^{18}$, R$^{30}$]-Ex-4-(1-30)—NH$_2$ | 57 | HGEGTFTSDLSKQAEEELVRLFIEWLKNGR—NH$_2$ |
| [A$^{14}$, I$^{19}$, R$^{30}$]-Ex-4-(1-30)—NH$_2$ | 58 | HGEGTFTSDLSKQAEEEAIRLFIEWLKNGR—NH$_2$ |
| [A$^{14,20}$, R$^{30}$]-Ex-4-(1-30)—NH$_2$ | 59 | HGEGTFTSDLSKQAEEEAVALFIEWLKNGR—NH$_2$ |
| [A$^{14}$, R$^{30}$, Y$^{22}$]-Ex-3-(1-30)—NH$_2$ | 60 | HSDGTFTSDLSKQAEEEAVRLYIEWLKNGR—NH$_2$ |
| [A$^{14}$, R$^{30}$, V$^{23}$]-Ex-4-(1-30)—NH$_2$ | 61 | HGEGTFTSDLSKQAEEEAVRLFVEWLKNGR—NH$_2$ |
| [A$^{14}$, L$^{24}$, R$^{30}$]-Ex-4-(1-30)—NH$_2$ | 62 | HGEGTFTSDLSKQAEEEAVRLFILWLKNGR—NH$_2$ |
| [A$^{14,25}$, R$^{30}$]-Ex-4-(1-30)—NH$_2$ | 63 | HGEGTFTSDLSKQAEEEAVRLFIEALKNGR—NH$_2$ |
| [A$^{14,26}$, R$^{30}$]-Ex-4-(1-30)—NH$_2$ | 64 | HGEGTFTSDLSKQAEEEAVRLFIEWAKNGR—NH$_2$ |
| [A$^{14,27}$, R$^{30}$]-Ex-4-(1-30)—NH$_2$ | 65 | HGEGTFTSDLSKQAEEEAVRLFIEWLANGR—NH$_2$ |
| [A$^{14,29}$, R$^{30}$]-Ex-4-(1-30)—NH$_2$ | 66 | HGEGTFTSDLSKQAEEEAVRLFIEWLKNAR—NH$_2$ |
| [A$^{14}$, R$^{30}$]-Ex-4-(1-30)—NH$_2$ | 67 | HGEGTFTSDLSKQAEEEAVRLFIEWLKNGR—NH$_2$ |
| [R$^{30}$]-Ex-3-(1-30)—NH$_2$ | 68 | HSDGTFTSDLSKQMEEEAVRLFIEWLKNGR—NH$_2$ |
| [Nle$^{14}$, Y$^{30}$]-Ex-3-(1-30)—NH$_2$ | 69 | HSDGTFTSDLSKQNleEEEAVRLFIEWLKNGY—NH$_2$ |
| [Nle$^{14}$, R$^{30}$]-Ex-3-(1-30)—OH | 70 | HSDGTFTSDLSKQNleEEEAVRLFIEWLKNGR—OH |
| [A$^{14}$, R$^{30}$]-Ex-3-(1-30)—NH$_2$ | 71 | HSDGTFTSDLSKQAEEEAVRLFIEWLKNGR—NH$_2$ |
| [Nla$^{14}$, R$^{30}$]-Ex-3-(2-30)—NH$_2$ | 72 | SDGTFTSDLSKQNleEEEAVRLFIEWLKNGR—NH$_2$ |
| [Nle$^{14}$, R$^{30}$]-Ex-3-(3-30)—NH$_2$ | 73 | DGTFTSDLSKQNleEEEAVRLFIEWLKNGR—NH$_2$ |
| Ac-[Nle$^{14}$, R$^{30}$]-Ex-3-(2-30)—NH$_2$ | 74 | Ac-DGTFTSDLSKQNleEEEAVRLFIEWLKNGR—NH$_2$ |
| Ac-[Nle$^{14}$, R$^{30}$]-Ex-3-(3-30)—NH$_2$ | 75 | Ac-DGTFTSDLSKQNleEEEAVRLFIEWLKNGR—NH$_2$ |
| [Nle$^{14}$]-Ex-3-(1-27)—NH$_2$ | 76 | HSDGTFTSDLSKQNleEEEAVRLFIELK—NH$_2$ |
| [K$^2$, P$^3$, A$^{14}$, R$^{30}$]-Ex-3-(1-30)—NH$_2$ | 77 | HKPGTFTSDLSKQAEEEAVRLFIEWLKNGR—NH$_2$ |
| [A$^2$, Nle$^{14}$, R$^{30}$]-Ex-3-(1-30)—NH$_2$ | 78 | HADGTFTSDLSKQNleEEEAVRLFIEWLKNGR—NH$_2$ |
| [C$^2$, Nle$^{14}$, R$^{30}$]-Ex-3-(1-30)—NH$_2$ | 79 | HCDGTFTSDLSKQNleEEEAVRLFIEWLKNGR—NH$_2$ |
| [D$^2$, Nle$^{14}$, R$^{30}$]-Ex-3-(1-30)—NH$_2$ | 80 | HDDGTFTSDLSKQNleEEEAVRLFIEWLKNGR—NH$_2$ |

-continued

| Exendin-Derivative | Seq. | Sequence |
|---|---|---|
| [E$^2$, Nle$^{14}$, R$^{30}$]-Ex-3-(1-30)—NH$_2$ | 81 | HEDGTFTSDLSKQNleEEEAVRLFIEWLKNGR—NH$_2$ |
| [F$^2$, Nle$^{14}$, R$^{30}$]-Ex-3-(1-30)—NH$_2$ | 82 | HFDGTFTSDLSKQNleEEEAVRLFIEWLKNGR—NH$_2$ |
| [G$^2$, Nle$^{14}$, R$^{30}$]-Ex-3-(1-30)—NH$_2$ | 83 | HGDGTFTSDLSKQNleEEEAVRLFIEWLKNGR—NH$_2$ |
| [H$^2$ Nle$^{14}$R$^{30}$]-Ex-3-(1-30)—NH$_2$ | 84 | HHDGTFTSDLSKQNleEEEAVRLFIEWLKNGR—NH$_2$ |
| [I$^2$, Nle$^{14}$, R$^{30}$]-Ex-3-(1-30)—NH$_2$ | 85 | HIDGTFTSDLSKQNleEEEAVRLFIEWLKNGR—NH$_2$ |
| [K$^2$, Nle$^{14}$, R$^{30}$]-Ex-3-(1-30)—NH$_2$ | 86 | HKDGTFTSDLSKQNleEEEAVRLFIEWLKNGR—NH$_2$ |
| [L$^2$, Nle$^{14}$, R$^{30}$]-Ex-3-(1-30)—NH$_2$ | 87 | HLDGTFTSDLSKQNleEEEAVRLFIEWLKNGR—NH$_2$ |
| [M$^2$, Nle$^{14}$, R$^{30}$]-Ex-3-(1-30)—NH$_2$ | 88 | HMDGTFTSDLSKQNleEEEAVRLFIEWLKNGR—NH$_2$ |
| [N$^2$Nle$^{14}$, R$^{30}$]-Ex-3-(1-30)—NH$_2$ | 89 | HNDGTFTSDLSKQNleEEEAVRLFIEWLKNGR—NH$_2$ |
| [P$^2$, Nle$^{14}$, R$^{30}$]-Ex-3-(1-30)—NH$_2$ | 90 | HPDGTFTSDLSKQNleEEEAVRLFIEWLKNGR—NH$_2$ |
| [Q$^2$, Nle$^{14}$, R$^{30}$]-Ex-3-(1-30)—NH$_2$ | 91 | HQDGTFTSDLSKQNleEEEAVRLFIEWLKNGR—NH$_2$ |
| [R$^2$, Nle$^{14}$, R$^{30}$]-Ex-3-(1-30)—NH$_2$ | 92 | HRDGTFTSDLSKQNleEEEAVRLFIEWLKNGR—NH$_2$ |
| [T$^2$, Nle$^{14}$, R$^{30}$]-Ex-3-(1-30)—NH$_2$ | 93 | HTDGTFTSDLSKQNleEEEAVRLFIEWLKNGR—NH$_2$ |
| [V$^2$, Nle$^{14}$, R$^{30}$]-Ex-3-(1-30)—NH$_2$ | 94 | HVDGTFTSDLSKQNleEEEAVRLFIEWLKNGR—NH$_2$ |
| [W$^2$, Nle$^{14}$, R$^{30}$]-Ex-3-(1-30)—NH$_2$ | 95 | HWDGTFTSDLSKQNleEEEAVRLFIEWLKNGR—NH$_2$ |
| [Y$^2$, Nle$^{14}$, R$^{30}$]-Ex-3-(1-30)—NH$_2$ | 96 | HYDGTFTSDLSKQNleEEEAVRLFIKWLKNGR—NH$_2$ |
| [A$^{3,14}$, R$^{30}$]-Ex-3-(1-30)—NH$_2$ | 97 | HSAGTFTSDLSKQAEEEAVRLFIEWLKNGR—NH$_2$ |
| [A$^{5,14}$, R$^{30}$]-Ex-3-(1-30)—NH$_2$ | 98 | HSDGAFTSDLSKQAEEEAVRLFIEWLKNGR—NH$_2$ |
| [A$^{14}$, R$^{30}$, Y$^5$]-Ex-3-(1-30)—NH$_2$ | 99 | HSDGYFTSDLSKQAEEEAVRLFIEWLKNGR—NH$_2$ |
| [A$^{14}$, R$^{30}$, Y$^6$]-Ex-3-(1-30)—NH$_2$ | 100 | HSDGTYTSDLSKQAEEEAVRLFIEWLKNGR—NH$_2$ |
| [A$^{14}$, I$^6$, R$^{30}$]-Ex-3-(1-30)—NH$_2$ | 101 | HSDGTITSDLSKQAEEEAVRLFIEWLKNGR—NH$_2$ |
| [A$^{14}$, R$^{30}$, S$^7$]-Ex-3-(1-30)—NH$_2$ | 102 | HSDGTFSSDLSKQAEEEAVRLFIEWLKNGR—NH$_2$ |
| [A$^{14}$, R$^{30}$, Y$^7$]-Ex-3-(1-30)—NH$_2$ | 103 | HSDGTFYSDLSKQAEEEAVRLFIEWLKNGR—NH$_2$ |
| [A$^{14}$, R$^{30}$, T$^8$]-Ex-3-(1-30)—NH$_2$ | 104 | HSDGTFTTDLSKQAEEEAVRLFIEWLKNGR—NH$_2$ |
| [A$^{14}$, R$^{30}$, Y$^8$]-Ex-3-(1-30)—NH$_2$ | 105 | HSDGTFTYDLSKQAEEEAVRLFIEWLKNGR—NH$_2$ |
| [A$^{14}$, E$^9$, R$^{30}$]-Ex-3-(1-30)—NH$_2$ | 106 | HSDGTFTSELSKQAEEEAVRLFIEWLKNGR—NH$_2$ |
| [A$^{10,14}$, R$^{30}$]-Ex-3-(1-30)—NH$_2$ | 107 | HSDGTFTSDASKQAEEEAVRLFIEWLKNGR—NH$_2$ |
| [A$^{11,14}$, R$^{30}$]-Ex-3-(1-30)—NH$_2$ | 108 | HSDGTFTSDLAKQAEEEAVRLFIEWLKNGR—NH$_2$ |
| [A$^{12,14}$, R$^{30}$]-Ex-3-(1-30)—NH$_2$ | 109 | HGEGTFTSDLSAQAEEEAVRLFIEWLKNGR—NH$_2$ |
| [A$^{13,14}$, R$^{30}$]-Ex-3-(1-30)—NH$_2$ | 110 | HSDGTFTSDLSKAAEEEAVRLFIEWLKNGR—NH$_2$ |
| [A$^{14,15}$, R$^{30}$]-Ex-3-(1-30)—NH$_2$ | 111 | HSDGTFTSDLSKQAEEEAVRLFIEWLKNGR—NH$_2$ |
| [A$^{14,17}$, K$^1$, R$^{30}$]-Ex-3-(1-30)—NH$_2$ | 112 | KSDGTFTSDLSKQAEEAAVRLFIEWLKNGR—NH$_2$ |
| [A$^{14}$, L$^{18}$, R$^{30}$]-Ex-3-(1-30)—NH$_2$ | 113 | HSDGTFTSDLSKQAEEELVRLFIEWLKNGR—NH$_2$ |
| [A$^{14}$, I$^{19}$, R$^{30}$]-Ex-3-(1-30)—NH$_2$ | 114 | HSDGTFTSDLSKQAEEEAIRLFIEWLKNGR—NH$_2$ |
| [A$^{14,20}$, R$^{30}$]-Ex-3-(1-30)—NH$_2$ | 115 | HSDGTFTSDLSKQAEEEAVALFIEWLKNGR—NH$_2$ |
| [A$^{14}$, R$^{30}$, Y$^{22}$]-Ex-3-(1-30)—NH$_2$ | 116 | HSDGTFTSDLSKQAEEEAVRLYIEWLKNGR—NH$_2$ |
| [A$^{14}$, R$^{30}$, V$^{23}$]-Ex-3-(1-30)—NH$_2$ | 117 | HSDGTFTSDLSKQAEEEAVRLFVEWLKNGR—NH$_2$ |
| [A$^{14}$, L$^{24}$, R$^{30}$]-Ex-3-(1-30)—NH$_2$ | 118 | HSDGTFTSDLSKQAEEEAVRLFILWLKNGR—NH$_2$ |
| Suc-[Nle$^{14}$, R$^{30}$]-Ex-3-(3-30)—NH$_2$ | 119 | Suc-DGTFTSDLSKQNleEEEAVRLFIEWLKNGR—NH$_2$ |
| [Nle$^{14}$, R$^{30}$]-Ex-3-(1-30)—NH$_2$ | 120 | HSDGTFTSDLSKQNleEEEAVRLFIEWLKNGR—NH$_2$ |

The following examples were synthesized in a 0.02 mmol batch by the solid phase method on RAM resin® (Rapp Polymere, Tübingen) in which aminomethylpolystyrene (1%)divinylbenzene is derivatized with Rink amide anchor (4-(2',4'-dimethoxyphenyl-aminomethyl)-phenoxy group) (loading: 0.5 mmol/g). The syntheses were carried out on a multiple automated peptide synthesizer SyRo II from the MultiSynTech Company (Bochum). The protected amino acids that were used were analogous to those of example 1. The protected amino acids were sequentially coupled in a 5-fold excess with single couplings of 40 minutes duration at 40° C. and while stirring. 2-(1H-benzotriazol-1-yl)-1,1,3,3-tetramethyluronium tetrafluoroborate (TBTU) with the addition of diisopropylethylamine was used as the activation reagent. The cleavage and purification of the peptide was carried out analogously to example 1. The yields, purities and analytical data of the peptides synthesized as described above are listed in the following two tables.

TABLE 1

| Seq. ID | Yield [mg] | Purity [%] | ESI-MS |
|---|---|---|---|
| 36 | 6.0 | 99 | 3343.3 |
| 38 | 12.8 | 99 | 3477.4 |
| 68 | 14.2 | 99 | 3523.4 |
| 69 | 14.1 | >99 | 3512.1 |
| 70 | 18.0 | 95 | 3506.0 |

TABLE 1-continued

| Seq. ID | Yield [mg] | Purity [%] | ESI-MS |
|---|---|---|---|
| 71 | 22.4 | 95 | 3463.6 |
| 72 | 6.6 | >99 | 3368.0 |
| 73 | 17.8 | >99 | 3281.1 |
| 75 | 12.0 | 99 | 3323.1 |
| 76 | 14.0 | 99 | 3178.1 |
| 77 | 7.2 | 99 | 3486.6 |
| 78 | 23.8 | 95 | 3488.1 |
| 79 | 19.0 | 95 | 3520.1 |
| 80 | 15.2 | 95 | 3531.9 |
| 81 | 8.6 | >99 | 3545.9 |
| 82 | 23.6 | 98 | 3563.9 |
| 83 | 25.4 | 95 | 3475.6 |
| 84 | 10.4 | >99 | 3554.1 |
| 85 | 8.2 | >99 | 3530.1 |
| 86 | 10.4 | 95 | 3545.3 |
| 87 | 9.2 | >99 | 3530.1 |
| 88 | 13.6 | >99 | 3548.1 |
| 89 | 10.6 | >99 | 3531.0 |
| 90 | 9.4 | 96 | 3514.9 |
| 91 | 6.0 | >99 | 3545.4 |
| 92 | 15.4 | >99 | 3574.9 |
| 93 | 10.1 | >99 | 3519.7 |
| 94 | 9.4 | >99 | 3517.7 |
| 95 | 12.0 | >99 | 3604.7 |
| 96 | 9.8 | 95 | 3581.8 |
| 120 | 8.5 | 95 | 3505.6 |

TABLE 2

Amino acid analyses

| Seq. ID | Ala | Arg | Asx | Glx | Gly | His | Ile | Leu | Lys | Nle | Phe | Ser | Thr | Trp | Val |
|---|---|---|---|---|---|---|---|---|---|---|---|---|---|---|---|
| 36[a] | 3.18 (3) | 0.99 (1) | 1.95 (2) | 3.04 (3) | 2.94 (3) | 0.89 (1) | 1.03 (1) | 2.14 (2) | 2.09 (2) | | 1.95 (2) | 3.06 (3) | 1.88 (2) | 0.99 (1) | 1.94 (2) |
| 38 | 2.08 (2) | 2.10 (2) | 2.00 (2) | 6.06 (6) | 2.04 (2) | 0.81 (1) | 1.01 (1) | 3.25 (3) | 2.13 (2) | | 1.96 (2) | 3.08 (3) | 1.82 (2) | 0.94 (1) | 1.02 (1) |
| 68[b] | 1.02 (1) | 2.14 (2) | 3.16 (3) | 5.06 (5) | 1.71 (2) | 0.93 (1) | 1.02 (1) | 3.21 (3) | 2.08 (2) | | 1.93 (2) | 3.00 (3) | 1.88 (2) | 0.98 (1) | 1.02 (1) |
| 69[c] | 1.02 (1) | 1.12 (1) | 2.99 (3) | 4.94 (5) | 1.81 (2) | 0.77 (1) | 1.12 (1) | 3.26 (3) | 2.12 (2) | 1.04 (1) | 1.99 (2) | 2.91 (3) | 1.81 (2) | 1.06 (1) | 1.03 (1) |
| 70 | 1.08 (1) | 2.15 (2) | 2.96 (3) | 5.07 (5) | 1.84 (2) | 0.85 (1) | 1.06 (1) | 3.23 (3) | 2.06 (2) | 0.92 (1) | 1.99 (2) | 2.01 (3) | 1.84 (2) | 1.05 (1) | 1.04 (1) |
| 71 | 1.99 (2) | 2.06 (2) | 3.14 (3) | 4.98 (5) | 1.95 (2) | 0.85 (1) | 1.01 (1) | 3.20 (3) | 2.08 (2) | | 1.94 (2) | 3.09 (3) | 1.90 (2) | 1.03 (1) | 0.96 (1) |
| 72 | 1.02 (1) | 2.12 (2) | 3.06 (3) | 5.02 (5) | 1.94 (2) | | 1.02 (1) | 3.25 (3) | 2.11 (2) | 0.95 (1) | 1.98 (2) | 2.92 (3) | 1.88 (2) | 1.02 (1) | 1.03 (1) |
| 73 | 1.01 (1) | 2.04 (2) | 3.02 (3) | 5.03 (5) | 1.83 (2) | | 0.99 (1) | 3.19 (3) | 2.07 (2) | 1.06 (1) | 1.98 (2) | 2.00 (2) | 1.87 (2) | 0.97 (1) | 1.03 (1) |
| 75 | 1.09 (1) | 2.21 (2) | 3.10 (3) | 5.18 (5) | 1.75 (2) | | 1.16 (1) | 3.26 (3) | 2.10 (2) | 1.08 (1) | 1.95 (2) | 2.10 (2) | 2.04 (2) | 1.28 (1) | 0.88 (1) |
| 76 | 1.03 (1) | 1.06 (1) | 2.05 (2) | 4.90 (5) | 0.94 (1) | 0.88 (1) | 1.03 (1) | 3.18 (3) | 2.01 (2) | 1.03 (1) | 1.95 (2) | 3.02 (3) | 1.86 (2) | 0.98 (1) | 1.03 (1) |
| 77[d] | 2.07 (2) | 2.00 (2) | 2.10 (2) | 5.07 (5) | 1.78 (2) | 0.93 (1) | 1.01 (1) | 3.14 (3) | 3.12 (3) | | 1.93 (2) | 2.05 (2) | 1.93 (2) | 1.01 (1) | 1.01 (1) |
| 78 | 2.11 (2) | 2.17 (2) | 3.14 (3) | 5.01 (5) | 1.92 (2) | 0.90 (1) | 1.06 (1) | 3.25 (3) | 2.06 (2) | 1.05 (1) | 1.99 (2) | 2.06 (2) | 1.90 (2) | 1.00 (1) | 1.05 (1) |
| 79[e] | 1.16 (1) | 2.10 (2) | 3.07 (3) | 5.07 (5) | 1.78 (2) | 0.66 (1) | 1.08 (1) | 3.30 (3) | 2.06 (2) | 0.96 (1) | 1.93 (2) | 2.02 (2) | 1.87 (2) | 1.06 (1) | 1.05 (1) |
| 80 | 1.07 (1) | 2.13 (2) | 3.78 (4) | 5.03 (5) | 1.82 (2) | 0.84 (1) | 1.05 (1) | 3.20 (3) | 2.04 (2) | 0.92 (1) | 1.97 (2) | 1.99 (2) | 1.82 (2) | 1.05 (1) | 1.03 (1) |
| 81 | 1.04 (1) | 2.06 (2) | 3.08 (3) | 5.96 (6) | 2.01 (2) | 0.82 (1) | 1.02 (1) | 3.17 (3) | 2.08 (2) | 0.95 (1) | 2.04 (2) | 2.05 (2) | 1.89 (2) | 1.01 (1) | 0.96 (1) |
| 82 | 1.09 (1) | 1.96 (2) | 3.01 (3) | 4.99 (5) | 1.89 (2) | 1.02 (1) | 1.02 (1) | 3.14 (3) | 2.04 (2) | 0.91 (1) | 2.74 (3) | 1.98 (2) | 1.85 (2) | 0.98 (1) | 0.99 (1) |
| 83 | 1.08 (1) | 2.22 (2) | 3.09 (3) | 5.01 (5) | 2.85 (3) | 0.83 (1) | 1.11 (1) | 3.23 (3) | 2.13 (2) | 1.12 (1) | 1.99 (2) | 2.09 (2) | 1.86 (2) | 0.99 (1) | 1.03 (1) |
| 84 | 1.01 (1) | 1.98 (2) | 3.09 (3) | 5.01 (5) | 1.71 (2) | 1.69 (2) | 1.07 (1) | 3.18 (3) | 2.07 (2) | 0.94 (1) | 1.99 (2) | 1.90 (2) | 1.84 (2) | 0.98 (1) | 1.01 (1) |
| 85 | 1.07 (1) | 2.12 (2) | 3.11 (3) | 5.03 (5) | 1.88 (2) | 0.93 (1) | 1.83 (2) | 3.23 (3) | 2.11 (2) | 1.11 (1) | 1.97 (2) | 2.03 (2) | 1.94 (2) | 0.97 (1) | 1.02 (1) |
| 86 | 1.03 (1) | 2.11 (2) | 3.07 (3) | 5.03 (5) | 2.10 (2) | 0.88 (1) | 1.11 (1) | 3.21 (3) | 3.00 (3) | 0.98 (1) | 1.97 (2) | 2.05 (2) | 1.88 (2) | 1.01 (1) | 0.99 (1) |
| 87 | 1.11 (1) | 2.16 (2) | 3.13 (3) | 5.03 (5) | 1.94 (2) | 0.89 (1) | 1.09 (1) | 4.05 (4) | 2.23 (2) | 0.93 (1) | 1.97 (2) | 2.07 (2) | 1.92 (2) | 0.95 (1) | 1.00 (1) |
| 88[f] | 1.03 (1) | 2.14 (2) | 3.16 (3) | 5.07 (5) | 1.71 (2) | 0.93 (1) | 1.02 (1) | 3.21 (3) | 2.09 (2) | 0.94 (1) | 1.93 (2) | 2.01 (2) | 1.88 (2) | 0.99 (1) | 1.02 (1) |
| 89 | 1.08 (1) | 1.97 (2) | 3.89 (4) | 5.06 (5) | 1.95 (2) | 0.88 (1) | 1.03 (1) | 3.19 (3) | 2.08 (2) | 0.92 (1) | 1.94 (2) | 2.03 (2) | 1.87 (2) | 0.99 (1) | 0.97 (1) |
| 90[g] | 1.00 (1) | 2.09 (2) | 3.18 (3) | 5.04 (5) | 1.97 (2) | 0.86 (1) | 1.02 (1) | 3.23 (3) | 2.10 (2) | 1.01 (1) | 1.96 (2) | 2.09 (2) | 1.92 (2) | 1.04 (1) | 0.97 (1) |
| 91 | 1.04 (1) | 2.08 (2) | 3.07 (3) | 5.73 (6) | 1.87 (2) | 0.80 (1) | 1.05 (1) | 3.21 (3) | 2.10 (2) | 1.05 (1) | 1.93 (2) | 1.95 (2) | 1.79 (2) | 1.11 (1) | 1.06 (1) |
| 92 | 1.01 (1) | 3.11 (3) | 3.02 (3) | 5.03 (5) | 1.83 (2) | 0.82 (1) | 0.99 (1) | 3.19 (3) | 2.07 (2) | 1.06 (1) | 1.97 (2) | 2.00 (2) | 1.87 (2) | 0.97 (1) | 1.03 (1) |
| 93 | 1.05 (1) | 2.12 (2) | 3.02 (3) | 5.04 (5) | 1.98 (2) | 0.82 (1) | 1.02 (1) | 3.28 (3) | 2.14 (2) | 1.00 (1) | 1.96 (2) | 2.06 (2) | 2.75 (3) | 0.95 (1) | 1.03 (1) |
| 94 | 1.07 (1) | 2.17 (2) | 3.04 (3) | 5.08 (5) | 1.72 (2) | 0.82 (1) | 1.14 (1) | 3.20 (3) | 2.06 (2) | 1.06 (1) | 1.92 (2) | 2.06 (2) | 2.00 (2) | 1.26 (1) | 1.72 (2) |
| 95 | 1.05 (1) | 2.18 (2) | 3.04 (3) | 5.04 (5) | 1.84 (2) | 0.80 (1) | 1.04 (1) | 3.31 (3) | 2.14 (2) | 0.95 (1) | 1.96 (2) | 2.02 (2) | 1.88 (2) | 1.76 (2) | 1.14 (1) |
| 96[h] | 1.03 (1) | 2.25 (2) | 3.03 (3) | 5.00 (5) | 1.84 (2) | 0.78 (1) | 1.14 (1) | 3.30 (3) | 2.15 (2) | 1.05 (1) | 2.02 (2) | 1.96 (2) | 1.84 (2) | 1.07 (1) | 1.05 (1) |
| 120 | 1.11 (1) | 1.98 (2) | 3.05 (3) | 5.06 (5) | 1.91 (2) | 1.03 (1) | 1.03 (1) | 3.18 (3) | 2.07 (2) | 0.93 (1) | 1.95 (2) | 2.94 (3) | 1.88 (2) | 0.99 (1) | 1.00 (1) |

[a] methionine 0.96 (1); tyrosine 0.86 (1)
[b] methionine 0.94 (1)
[c] tyrosine 0.82 (1)
[d] proline 1.02 (1)
[e] cysteine could not be detected under the given hydrolysis conditions
[f] methionine 0.93 (1)
[g] proline 0.86 (1)
[h] tyrosine 0.87 (1)

EXAMPLE 10

Pharmacological Data

Peptide Metabolism in Ectopeptidase Preparations or in Kidney Microvilli Membrane Preparations Background A group of ectopeptidases is responsible for the post-secretory metabolism of peptide hormones. These enzymes are bound to the plasma membranes of various cell types. Their active site is oriented towards the extracellular space. In addition these enzymes are present in high concentrations in the brush border membranes of the proximal renal tubuli. Renal brush border microvilli membranes (BBM) are therefore a suitable source for the relevant ectopeptidases and can be used as an in vitro test for the metabolic stability of synthetic peptides. Alternatively it is possible to use ectopeptidase preparations. The human neutral endopeptidase 24.11 as well as dipeptidyl peptidase IV were used as examples since GLP-1 is a substrate of both these ectopeptidases.

Preparation of Brush Border Microvilli Membranes

Microvilli membranes of the rat and pig kidney cortex are isolated by means of subcellular fractionation using the differential centrifugation method (Booth and Kenny (1975)). 4 Brush border ectopeptidases are examined fluorimetrically and other marker enzymes are measured colorimetrically in order to assess the degree of purity and the yield of membranes.

Ectopeptidase Preparations

Purified human neutral endopeptidase 24.11 was obtained in a recombinant form from Genentech (San Francisco, USA), dipeptidyl peptidase IV was obtained as an isolate from human placenta from Calbiochem (Bad Soden).

Incubation Protocol

Microvilli membranes (0.5–1 $\mu$g protein) or the respective ectopeptidase preparation (60–300 ng) were incubated with 10 $\mu$g peptide (about 3 nmol) in 100 $\mu$l HEPES buffer (50 mM, pH 7.4) which contained 50 mM NaCl. The reactions were terminated at predetermined times (duration up to 1 hour) by boiling. Subsequently the samples were centrifuged (10,000×g), diluted with 150 $\mu$l 0.1% TFA and analysed by means of reversed phase (RP) HPLC. Each sample was determined in duplicate.

HPLC Analysis

A system with the following components was used for HPLC analysis: A 2248 low pressure pump (Pharmacia-LKB, Freiburg), a WISP 10B autoinjector (Millipore-Waters, Eschborn), a UV detector SP-4 (Gynkotec, Berlin), a low pressure mixing system (Pharmacia-LKB, Freiburg) and a program manager software control (Pharmacia-LKB, Freiburg). The separations were carried out over Lichrospher C-8, 5 $\mu$, 4×124 mm (Merck, Darmstadt) with a binary gradient using the mobile solvents A: 0.1% trifluoroacetic acid (TFA) and B: acetonitrile:water:TFA (70:29:0.1). After injection of 244 $\mu$l of the sample solution onto a column equilibrated with the motile solvent A, the incubation products were eluted with a linear gradient of 0% to 80% B in 80 min and detected at 215 nm UV absorption.

Calculation of the Proteolysis Rates

Two measurements were carried out for each incubation period of each peptide and the average peak height of the substrate peak was plotted versus time. Using GLP-1 as an example it was possible to show that the peak height is linearly proportional to the quantity of the peptide in the sample solution. Furthermore a linear decrease of the peak height with time was observed within the first hour of incubation with the microvilli membranes or the peptidases. Hence the proteolysis rate is determined from the decrease in the height of the substrate peak and is expressed as [$\mu$mol substrate/mg protein/minute].

Degradation Stability of Exendin Analogues

Incubation With Human Neutral Endopeptidase 24.11b

[Nle$^{14}$,Arg$^{30}$]-exendin-4-(1–30)-NH$_2$ (SEQ ID No. 3) was incubated with the neutral endopeptidase 24.11 as described above and the degradation rate was determined. GLP-1-(7–36)-NH$_2$ served as a control. The results are shown in Table 3.

TABLE 3

Incubations with dipeptidyl peptidase IV

| | Degradation rate [mM/100 ng/ml NEP24.11/min] |
|---|---|
| GLP1-(7-36)-NH$_2$ | 0.0586 |
| [Nle$^{14}$,Arg$^{30}$]-Ex-4-(1-30)-NH$_2$ Exmp. 1 | 0.0083 |

The peptides listed in Table 4 were incubated with dipeptidyl peptidase IV (DDP-IV) as described above. Each of the incubations was terminated at the time when the GLP-1-(7–36)-NH$_2$ exhibited 50% hydrolysis. The substrate peak of each peptide was collected from the rpHPLC run and examined by mass spectroscopy in order to exclude truncated products.

TABLE 4

Incubations with brush border microvilli membranes

| Analogue | Seq. ID | Substrate for DDP-IV |
|---|---|---|
| [Ala$^2$,Nle$^{14}$,Arg$^{30}$]-Ex-3-(1-30)-NH$_2$ | 78 | no proteolysis |
| GLP1-(7-36)-NH$_2$ | | 50% proteolysis |

The proteolysis rates which were calculated after incubation with brush border microvilli membranes (BBM) by the protocol described above are shown in Table 5. GLP-1-(7–36)-NH$_2$ served as a control.

TABLE 5

Insulin secretion by isolated islet cells

| Analogue | Seq. ID | Degradation rate [ng peptide/min/mg BBM] |
|---|---|---|
| GLP1-(7-36)-NH$_2$ | | 880.00 |
| [Lys$^2$,Nle$^{14}$,Arg$^{30}$]-Ex-3-(1-30)-NH$_2$ | 86 | 2.05 |

Organ Removal

The abdomen of anaesthetised (0.3–0.5 ml nembutal/isotonic saline solution 1:4 i.p.) mice is opened by a median incision and two side incisions, the peritoneum is immobilized and cut open at the costal arch along the diaphragm. All organs are inflated and stained red by injection of a neutral red solution into the left ventricle. The pancreas is carefully removed along the stomach and duodenum up to the mesenteries. Until digestion the pancreas is placed in an ice-cooled petri dish in Hank's balanced salt solution (HBBS) and a few drops of neutral red.

Islet Preparation

Two pancreases are dabbed with cellulose, placed in a tube, 5 ml freshly prepared collagenase solution (collagenase (Cl. histolyticum) 0.74 U/mg, Serva, 2 mg/ml in HBBS/water 1:9, pH 7.4) is added and they are incubated for 18 minutes at 37° C. while shaking. Subsequently a centrifugation is carried out at 1000 rpm for 1 minute. The supernatant is discarded, In a second digestion step 5 ml collagenase solution (1 mg/ml) is incubated for 4 minutes, shaken and undigested tissue is sedimented. The supernatant is decanted and the whole process is repeated four to five times. The supernatant is then centrifuged for 1 minute at 1000 rpm and the collagenase solution is discarded. The remaining pellet is shaken with ice-cold HBBS and sedimented for ca. 10 minutes on ice. This wash process is repeated for a further three times. The faint pink stained islets are picked out from the washed pellets under a stereoscopic magnifying glass and transferred to culture medium (100 ml RPMI 1640 (Gibco), 1 ml glutamine, 1 ml penicillin, 1 ml Cibrobay antibiotic (Bayer), 10 ml foetal calf serum, 2 ml Hepes buffer 1 M). In order to obtain the purest possible culture, the islets are picked two to three times and transferred to fresh culture medium.

Stimulation of the Islets

The islet cells from the culture medium are distributed in Eppendorff vessels containing 200 ml stimulation buffer (118 mM NaCl, 0.2 mM $NaH_2PO^4$, 0.565 mM $MgCl^2$, 1.25 mM $CaCl^2$, 4.1 mM KCl, 10 mM Hepes, 1% BSA, 3.3 mM glucose; pH 7.4) in a quantity of 10 islets per Eppendorff vessel and placed in an incubator for 1 hour at 37° C. Subsequently the peptides to be tested are added and filled up to 500 ml with stimulation buffer and incubated for one hour at 37° C. The islets are centrifuged at 1000 rpm for 1 minute. The amount of C-peptide is measured in the supernatant using an insulin-RIA (DPC Biermann, Nauheim). Each test substance was determined in quadruplicate.

Activity of the Exendin Analogues

Some exendin analogues were tested as described above on isolated islet cells for insulin secretory activity. The data are shown as an example in the following table.

Insulin Release From Isolated Islets After 1 Hour [mIU/h/10 Islets] in the Presence of 10 mM Glucose:

TABLE 6

|  | Control | GLP1-(7-36)-$NH_2$ | Seq. ID 84 |
| --- | --- | --- | --- |
| 10 mM glucose | 30.21 |  |  |
| $10^{-7}$ (10 mM glucose) |  | 53.52 | 48.94 |
| $10^{-8}$ (10 mM glucose) |  | 42.78 | 41.72 |
| $10^{-9}$ (10 mM glucose) |  | 29.99 | 38.76 |
| $10^{-10}$ (10 mM glucose) |  |  | 35.05 |

Measurement of the Increase of the Cytosolic Calcium Concentration in B Cells of the Endocrine Pancreas (Clonal B Cell Line INS-1)

Culture of INS-1-cells (Asfari, M., 1992):

INS-1 cells are cultured in RPMI 1640 medium containing 10% FCS, 10 mM HEPES buffer (pH 7.4), 2 mM L-glutamine, 100 i.U. penicillin/ml, 100 µg streptomycine/ml, 1 mM pyruvate (sodium salt) and 50 µM 2-mercaptoethanol at 37° C. in an atmosphere of 95% air and 5% $CO_2$. After 6 to 8 days growth on plastic cell culture plates, the subconfluent cells, after rinsing once with PBS (phosphate-buffered saline), are detached from the base by incubating for four minutes at 37° C. with 0.025% trypsin and 0.27 mM EDTA in isoosmotic saline solution Preparation of the Cells for Calcium Measurements:

The detached cells are resuspended in Spinner medium (culture medium as above, but containing 5% FCS and 25 mM HEPES) and incubated for two and a half hours in a Spinner bottle with a stirrer bar. Afterwards the medium is removed by centrifugation and the cells are resuspended in Spinner medium. They are then incubated for 30 minutes at 37° C. with 2 µM Fura-2/acetoxymethyl ester under the same conditions as before. The Fura loading of the cells is terminated by washing the cells once Spinner medium (room temperature). Afterwards the cells are resuspended in spinner medium at room temperature ($2 \times 10^7$ cells/ml). The cells are then removed from this suspension for calcium measurements.

Measurements of the Cytosolic Calcium Concentration:

The measurements are carried out at 37° C. in a modified Krebs-Ringer buffer (KRBH) containing 136 mM NaCl, 4.8 mM KCl, 2 mM $CaCl_2$, 1.2 MM $MgSO_4$, 1.2 mM $KH_2PO_4$, 5 mM $NaNCO_3$, 10 mM glucose, 250 µM sulfinpyrazone (to inhibit the Fura-2 efflux into the medium) and 25 mM HEPES buffer (adjusted to pH 7.4 with NaOH). The cell concentration is $1-2 \times 10^6$/ml. The measurements are carried out in a cuvette stirred with a stirring bar in a spectrofluorimeter at 37° C. with 1.5 ml cell suspension. The excitation wavelength is 340 nm, the emission wavelength is 505 nm. At the end of the measurement 50 µM $MnCl_2$ is added which is followed by 100 µm DTPA (diethylenetriamine pentaacetate) in order to determine the proportion of extracellular fluorescence indicator relative to the measured fluorescence by temporarily quenching the fluorescence of extracellular Fura. After the addition of DTPA the entire Fura is firstly converted into a calcium-saturated and then into a calcium-free state to determine the calibration values $F_{max}$ (calcium-saturated) and $F_{min}$ (calcium-free) for the respective measurement. For this purpose the cells are lysed by adding 0.1% Triton X-100. The dye is saturated with calcium by contact with the high extracellular calcium concentration. Subsequently 5 mM EGTA (ethylenebis (oxyethylenenitrilo)-tetraacetate) and 20 mM Tris solution are added in order to completely convert the dye into the calcium-free form.

The cytosolic calcium ion concentration is calculated according to the algorithm introduced by R. Tsien and colleagues (Grynkiewicz, G., 1985):

$$[Ca^{2+}]_{cyt} = ((F - F_{min})/(F_{max} - F)) \times K_D$$

(F: fluorescence of the respective measurement point; KD: dissociation constant of the calcium complex of Fura-2, 225 nM (Grynkiewicz, G., 1985)).

(Before this calculation a compensation is carried out for the presence of extracellular Fura. For this the fluorescence quantity (extracellular Fura) determined by manganese addition is firstly subtracted from the fluorescence values of the measurement points. Then $F_{max}$ is corrected by substracting this quantity. Finally the correction value for $F_{min}$ is determined. For this purpose the fluorescence quantity determined by addition of manganese is divided by the value 2.24. The value 2.24 was determined as the intrinsic instrument proportionality factor between the fluorescence of calcium-saturated and calcium-free Fura-2 at an excitation wavelength of 340 nm (measured with unesterified, free Fura-2). The correction value obtained in this manner was subtracted from $F_{min}$).

The examined peptides were added as 1000-fold concentrated solutions ($10^{-5}$ M) in KRBH without $CaCl_2$ and glucose.

Activity of the Exendin Analogues

Several exendin analogues were tested in the calcium assay on INS-1 cells as described above for their biolotical activity. The data are shown as an example in FIG. 1 as well as in Table 7.

TABLE 7

| SEQ. ID Nr. | Concentration of the peptides $10^{-8}$ M | $\Delta[Ca^{2+}]$cyt ± SD (n = 4) |
|---|---|---|
| 6 | [Arg$^{30}$]-exendin-(1-30)-NH$_2$ | 64 ± 8 nM |
| 3 | [Nle$^{14}$,Arg$^{30}$]-exendin-(1-30)-NH$_2$ | 63 ± 8 nM |
| 8 | [Ala$^{21}$,Arg$^{30}$]-exendin-(1-30)-NH$_2$ | 61 ± 11 nM |
| 9 | [Ala$^{28}$,Arg$^{30}$]-exendin-(1-30)-NH$_2$ | 65 ± 15 nM |
| 10 | [Ala$^{21,28}$,Arg$^{30}$]-exendin-(1-30)-NH$_2$ | 69 ± 30 nM |
|  | Control: GLP-1-(7-36) amide | 65 ± 10 nM |

Competition With GLP-1-(7–36)-NR$_2$ on B Cells of the Endocrine Pancreas (Clonal B Cell Line INS-1)
  Culture of INS-1-cells (Asfari, M., 1992)
  See measurement of calcium concentration
  Competition Experiments
  The detached cells are taken up and suspended in Krebs-Ringer buffer (25 mM Tris, 120 mM NaCl, 1.2 mM MgSO$_4$, 5 mM KCl, 1 mM Na-EDTA, 15 mM CH$_3$COONa adjusted to pH 7.4 and supplemented with 1% HSA and 0.1% bacitracin). 250 ml is removed each time from this suspension for a reaction mixture, admixed with 20 ml tracer ($^{125}$I-GLP1-(7–36)-NH$_2$, 20,000 cpm) and 30 ml of the peptide to be examined in the corresponding dilution. Subsequently it is incubated for 30 minutes at 37° C., centrifuged for 4 minutes at 13,000 rpm, washed three times with buffer and the radioactivity bound to the pellet (γ-counter) is measured. Competition curves were obtained by incubation with 10 different dilutions of the peptide to be tested ($10^{-10}$–$10^{-6}$ M in Krebs-Ringer buffer).
  Receptor Affinity of the Exendin Analogues
  The data are shown as an example in Table 8. GLP-1-(7-NH$_2$ served as a standard.

TABLE 8

| Seq. ID | peptide | Kd$_{GLP1}$ ± SD [nM] | Kd ± SD [nM] | Kd/Kd$_{GLP1}$ |
|---|---|---|---|---|
| 69 | [Nle$^{14}$,Tyr$^{30}$]-Ex3-(1-30)-NH$_2$ | 1.04 ± 0.05 | 0.56 ± 0.08 | 0.5 |

Literatur

Albericio, F. and Barany, G. (1987) *Int. J. Peptide Protein Res.* 30, 206–216.
Asfari, M., Janjic, D., Meda, P., Li, G., Halban, P. A. and Wollheim, C. B. (1992) *Endocrinology* 130, 167–178.
Barlos, K., Gatos, D., Kapolos, S., Paphotiu, G., Schafer, W., and Wengqing, Y. (1989) *Tetrahedron Lett.* 30, 3947–3950.
Booth, and Kenny, (1975) *Biochem. J.* 142, 575–581.
Eng, J., Andrews, P. C., Kleinman, W. A., Singh, L., and Raufman, J.-P. (1990) *J. Biol. Chem.* 265, 20259–20262.
Eng, J., Andrews, P. C., Kleinman, W. A., Singh, L., Singh, G., and Raufman, J.-P. (1992) *J. Biol. Chem.* 267, 7402–7405.
Fehmann, H. C., Göke, R., Göke, B., Bachle, R., Wagner, B. and Arnold, R. (1991) *Biochim. Biophys. Acta* 1091, 356–63.
Göke, R., Wagner, B., Fehmann, H. C. and Göke, B. (1993a) *Res. Exp. Med. Berl.* 193, 97–103
Göke, R., Fehman, H. C., Linn, T., Schmidt, H., Eng, J. and Göke, B. (1993b) *J. Biol. Chem.* 268, 19650–19655.
Grynkiewicz, G., Poenie, M. and Tsien, R. Y. (1985) *J. Biol Chem* 260, 3440–3450.
Gutniak, M., Orskov, C., Holst, J. J., Ahren, B. and Efendic, S. (1992) *N. Engl. J. Med.* 326, 1316–1322.
Komatsu, R., Matsuyama, T., Namba, M., Watanabe, N., Itoh, H., Kono, N. and Tarui, S. (1989) *Diabetes* 38, 902–905.
Kreymann, B., Williams, G., Ghatei, M. A. and Bloom, S. R. (1987) *Lancet* 2(8571), 1300–1304.
Nathan, D. M., Schreiber, E., Fogel, H., Mojsov, S. and Habener, J. F. (1992) *Diabetes Care* 15, 270–276.
Nauck, M. A., Kleine, N. Orskov, C., Holst, J. J., Willms, B. and Creutzfeld, W. (1993a) *Diabetologia* 36, 741–744.
Nauck, M. A., Heimesaat, M. M., Orskov, C., Holst, J. J., Ebert, R. and Creutzfeld, W. (1993b) *J. Clin. Invest.* 91, 301–307.
Raufman, J. P., Singh, L., Singh, G. and Eng, J., (1992) *J. Biol. Chem.* 267, 21432–21437.
Rink, E. (1987) *Tetrahedron Lett.* 28, 3787–3790.
Thorens, B., Porret, A., Buehler, L., Deng, S. P., Morel, P. and Widman, C. (1993) *Diabetes* 42, 1678–1682.
Wang, S. S. (1973) *J. Am. Chem. Soc.* 95, 1328–1333.

What is claimed is:

1. A peptide consisting essentially of SEQ ID NO:1 or SEQ ID NO:2

```
                                        SEQ ID NO:1
1               5                   10
His Ser Asp Gly Thr Phe Thr Ser Asp Leu Ser Lys Gln 15                  20                  25
Met Glu Glu Glu Ala Val Arg Leu Phe Ile Glu Trp Leu

30
Lys Asn Gly Xaa

SEQ ID NO:2
1               5                   10
His Gly Glu Gly Thr Phe Thr Ser Asp Leu Ser Lys Gln 15                  20                  25
Met Glu Glu Glu Ala Val Arg Leu Phe Ile Glu Trp Leu

30
Lys Asn Gly Xaa
``` in which Xaa specifies one of the proteinogenic amino acids: Asp, Glu, Arg, His, Lys, Ala, Asn, Cys, Gln, Ile, Leu, Met, Phe, Pro, Ser, Thr, Trp, Tyr, Val or a non-proteinogenic amino acid, and wherein in positions 1, 2, 28, 29 or 30, independent of one another, amino acids are optionally part of the sequence, and the N-terminus is represented by $NR_1R_2$ in which $R_1$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, $R_2$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, and the C-terminus is represented by $COR_3$ in which $R_3$ equals $OR_4$ or $NR_4R_5$ in which $R_4$ equals hydrogen or $C_1$–$C_6$ alkyl in which $R_5$ equals hydrogen or $C_1$–$C_6$ alkyl, as well as physiologically tolerated salts and esters of the foregoing.

2. A peptide as claimed in claim 1, wherein the Xaa amino acid at position 30 in SEQ ID NO:1 or SEQ ID NO:2 is Arg, D-Arg, Tyr or D-Tyr.

3. A peptide as claimed in claim 2, wherein the Xaa amino acid at position 30 in SEQ ID NO:1 or SEQ ID NO:2 is Arg or Tyr.

4. A peptide as claimed in claim 1, in which Xaa specifies one of the non-proteinogenic amino acids amino acids Dab, Dap, Om, β-Ala, Aib, Cit, Cha, Oak, Mab, Pab, Amb, Ahx, Ahp, Aoc, Ade, Atd, Nal, Nle, Sar, Tic.

5. A peptide consisting essentially of SEQ ID NO:1 or SEQ ID NO:2 wherein the peptide has one of the sequences identified by sequence ID NOS. 5, 68, 69, 71, 78–82 or 84–91, and wherein the N-terminus is represented by $NR_1R_2$ in which $R_1$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, $R_2$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, and the C-terminus is represented by $COR_3$ in which $R_3$ equals $OR_4$ or $NR_4R_5$ in which $R_4$ equals hydrogen or $C_1$–$C_6$ alkyl in which $R_5$ equals hydrogen or $C_1$–$C_6$ alkyl as well as physiologically tolerated salts and esters thereof.

6. A pharmaceutical preparation for stimulating the release of insulin comprising at least one peptide as claimed in claim 1, in addition to physiologically acceptable carriers and auxiliary substances.

7. A pharmaceutical composition comprising peptides as claimed in claim 1 for the treatment of diabetes.

8. A method of stimulating the release of insulin in a mammal comprising administering to the mammal a peptide according to claim 1 in an amount sufficient to release insulin.

9. The method of claim 8, wherein the mammal is a human.

10. A peptide consisting essentially of SEQ ID NO:1 or SEQ ID NO:2

```
                                              SEQ ID NO:1
1               5                   10
His Ser Asp Gly Thr Phe Thr Ser Asp Leu Ser Lys Gln 15                  20                  25
Met Glu Glu Glu Ala Val Arg Leu Phe Ile Glu Trp Leu

30
Lys Asn Gly Xaa

SEQ ID NO:2
1               5                   10
His Gly Glu Gly Thr Phe Thr Ser Asp Leu Ser Lys Gln 15                  20                  25
Met Glu Glu Glu Ala Val Arg Leu Phe Ile Glu Trp Leu

30
Lys Asn Glu Xaa
``` in which Xaa specifies one of the proteinogenic amino acids: Asp, Glu, Arg, His, Lys, Ala, Asn, Cys, Gln, Ile, Leu, Met, Phe, Pro, Ser, Thr, Trp, Tyr, Val or a non-proteinogenic amino acid, and wherein in positions 1, 2, 28, 29 or 30, independent of one another, amino acids are optionally part of the sequence, and the N-terminus is represented by $NR_1R_2$ in which $R_1$ denotes hydrogen, acetyl, trifluoroacetyl, adamantyl, Fmoc, benzyloxycarbonyl Boc, Alloc, $C_1$–$C_6$ alkyl, $C_2$–$C_8$ alkenyl or $C_7$–$C_9$ aralkyl, $R_2$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, and the C-terminus is represented by $COR_3$ in which $R_3$ equals $OR_4$ or $NR_4R_5$ in which $R_4$ equals hydrogen or $C_1$–$C_6$ alkyl
in which $R_5$ equals hydrogen or $C_1$–$C_6$ alkyl as well as physiologically tolerated salts and esters thereof, with the proviso that at least one but at most 10 of the following modifications (a) to (o) apply to the amino acid chain:

(a) the α-amino acid in position 1 is D-His, Ala, D-Ala, Gly, Lys or D-Lys;

(b) the α-amino acid in position 2 is Ser, D-Ser, Thr, D-Thr, Ala, D-Ala, Ile, D-Ile, Val, D-Val, Leu, or D-Leu, Cys, Asp, Glu, Phe, His, Lys, Met, Asn, Pro, Gln, Arg, Trp or Tyr;

(c) the α-amino acid in position 3 is D-Glu, D-Asp, Ala or D-Ala;

(d) the amino acid in position 4 is Ala, D-Ala or β-Ala;

(e) the α-amino acid in position 5 is Ser, Tyr or Ala;

(f) the α-amino acid in position 6 is Ala, Ile, Val, Leu, Cha or Tyr;

(g) the α-amino acid in position 7 is Ala, D-Ala, Tyr, D-Tyr, Ser, D-Ser or D-Thr;

(h) the α-amino acid in position 8 is Ala, Tyr or Thr;

(i) the α-amino acid in position 9 is Ala, D-Ala, Glu, D-Glu or D-Asp;

(j) the amino acids in positions 10, 11, 12, 15, 16, 17, 18, 19, 20, 21, 24, 28, 29 are, independent of one another, one of the above-specified proteinogenic amino acids which are different from the amino acid already present in the respective position(s) in SEQ ID NO:1 or SEQ ID NO:2 or a non-proteinogenic D- or L-amino acid;

(k) the α-amino acid in position 13 is a neutral L-amino acid except Gln:

(l) the α-amino acid in position 14 is replaced by a neutral L- or D-amino acid, except Met or L-leucine;

(m) the α-amino acid in position 22 is D-Phe, Tyr, D-Tyr, Leu, D-Leu, Val, D-Val, L-Cha, D-Cha, β-1-Nal, β-2-Nal or β-1-D-Nal;

(n) the α-amino acid in position 23 is Leu, D-Leu, D-Ile, Val, D-Val, L-Cha, D-Cha, Tyr, D-Tyr, Phe or D-Phe; and (o) the α-amino acid in positions 25, 26 or 27 is a neutral L- or D-amino acid, except Trp for position 25, Leu for position 26 and Lys for position 27.

11. A peptide as claimed in claim 10, wherein in SEQ ID NO:1 or SEQ ID NO:2 the α-amino acid in position 1 is Ala, Gly or Lys.

12. A peptide as claimed in claim 10, wherein in SEQ ID NO:1 or SEQ ID NO:2 the α-amino acid in position 2 is Thr, Ala, Val, Ile or Leu.

13. A peptide as claimed in claim 10, wherein in SEQ ID NO:1 or SEQ ID NO:2 the α-amino acid in position 3 is Ala.

14. A peptide as claimed in claim 10, wherein in SEQ ID NO:1 or SEQ ID NO:2 the α-amino acid in position 4 is Ala.

15. A peptide as claimed in claim 10 wherein in SEQ ID NO:1 or SEQ ID NO:2 the α-amino acid in position 6 is Ala, Ile, Val, Leu or Tyr.

16. A peptide as claimed in claim 10, wherein in SEQ ID NO:1 or SEQ ID NO:2 the α-amino acid in position 7 is Ala, Tyr or Ser.

17. A peptide as claimed in claim 10, wherein in SEQ ID NO:1 or SEQ ID NO:2 the α-amino acid in position 9 is Ala or Glu.

18. A peptide as claimed in claim 10 wherein in SEQ ID NO:1 or SEQ ID NO:2 the α-amino acid in positions 10, 11, 12, 15, 16, 17, 18, 19, 20, 21, 24, 28, 29 is a proteinogenic L-amino acid.

19. A peptide as claimed in claim 10, wherein in SEQ ID NO:1 or SEQ ID NO:2 the α-amino acid in position 13 is a neutral proteinogenic L-amino acid.

20. A peptide as claimed in claim 10, wherein in SEQ ID NO:1 or SEQ ID NO:2 the α-amino acid in position 14 is Nle, D-Nle, Ala, D-Ala, Ile, D-Ile, Val or D-Val.

21. A peptide as claimed in claim 10, wherein in SEQ ID NO:1 or SEQ ID NO:2 the α-amino acid in position 14 is Ile, Val or Ala.

22. A peptide as claimed in claim 10, wherein in SEQ ID NO:1 or SEQ ID NO:2 the α-amino acid in position 22 is Tyr, Leu or Val.

23. A peptide as claimed in claim 10, wherein in SEQ ID NO:1 or SEQ ID NO:2 the α-amino acid in position 23 is Leu, Val, Tyr or Phe.

24. A peptide as claimed in claim 10, wherein in SEQ ID NO:1 or SEQ ID NO:2 the α-amino acid in positions 25, 26 or 27 is a proteinogenic L-amino acid.

25. Peptide as claimed in claim 10, wherein in SEQ ID NO:1 or SEQ ID NO:2 an amino acid has been substituted at position 2.

26. Peptide as claimed in claim 10, wherein in SEQ ID NO:1 or SEQ ID NO:2 an amino acid has been substituted at position 14.

27. Peptide as claimed in claim 10, wherein in SEQ ID NO:1 or SEQ ID NO:2 an amino acid has been substituted at position 3.

28. A peptide of 25–30 amino acids in length having at least 25 contiguous amino acids of SEQ ID NO:1 or SEQ ID NO:2

```
                                        SEQ ID NO:1
1                   5                   10
His Gly Glu Gly Thr Phe Thr Ser Asp Leu Ser Lys Gln 15                  20                  25
Met Glu Glu Glu Ala Val Arg Leu Phe Ile Glu Trp Leu

30
Lys Asn Glu Xaa

SEQ ID NO:2
1                   5                   10
His Gly Glu Gly Thr Phe Thr Ser Asp Leu Ser Lys Gln 15                  20                  25
Met Glu Glu Glu Ala Val Arg Leu Phe Ile Glu Trp Leu

30
Lys Asn Glu Xaa
``` in which Xaa specifies one of the proteinogenic amino acids: Asp, Glu, Arg, His, Lys, Ala, Asn, Cys, Gln, Ile, Leu, Met, Phe, Pro, Ser, Thr, Trp, Tyr, Val or a non-proteinogenic amino acid, and wherein in positions 1, 2, 28, 29 or 30, independent of one another, amino acids are optionally part of the sequence, and the N-terminus is represented by $NR_1R_2$ in which $R_1$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, $R_2$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, and the C-terminus is represented by $COR_3$ in which $R_3$ equals $OR_4$ or $NR_4R_5$ in which $R_4$ equals hydrogen or $C_1$–$C_6$ alkyl in which $R_5$ equals hydrogen or $C_1$–$C_6$ alkyl, as well as physiologically tolerated salts and esters of the foregoing.

29. A peptide as claimed in claim 28, wherein the α amino acid at position 30 in SEQ ID NO:1 or SEQ ID NO:2 is Arg, D-Arg, Tyr or D-Tyr.

30. A peptide as claimed in claim 28, in which Xaa specifies one of the non-proteinogenic amino acids amino acids Dab, Dap, Orn, β-Ala, Aib, Cit, Cha, Oak, Mab, Pab, Amb, Ahx, Ahp, Aoc, Ade, Atd, Nal, Nle, Sar, Tic.

31. Pharmaceutical preparation for stimulating the release of insulin comprising at least one peptide as claimed in claim 28, in addition to physiologically acceptable carriers and auxiliary substances.

32. A pharmaceutical composition comprising peptides as claimed in claim 28 for the treatment of diabetes.

33. A peptide of 25–30 amino acids in length wherein the peptide has one of the sequences identified by SEQ ID NO:'S 5, 68, 69, 71, 78–82 or 84–91, and wherein the N-terminus is represented by $NR_1R_2$ in which $R_1$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, $R_2$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, and the C-terminus is represented by $COR_3$ in which $R_3$ equals $OR_4$ or $NR_4R_5$ in which $R_4$ equals hydrogen or $C_1$–$C_6$ alkyl in which $R_5$ equals hydrogen or $C_1$–$C_6$ alkyl as well as physiologically tolerated salts and esters thereof.

34. A peptide of 25–30 amino acids in length and having at least 25 contiguous amino acids derived from SEQ ID NO:1 or SEQ ID NO:2

```
                                        SEQ ID NO:1
1                   5                   10
His Gly Glu Gly Thr Phe Thr Ser Asp Leu Ser Lys Gln 15                  20                  25
Met Glu Glu Glu Ala Val Arg Leu Phe Ile Glu Trp Leu

30
Lys Asn Glu Xaa
``` or

```
                                        SEQ ID NO:2
1                   5                   10
His Gly Glu Gly Thr Phe Thr Ser Asp Leu Ser Lys Gln 15                  20                  25
Met Glu Glu Glu Ala Val Arg Leu Phe Ile Glu Trp Leu

30
Lys Asn Glu Xaa
``` in which Xaa specifies one of the proteinogenic amino acids: Asp, Glu, Arg, His, Lys, Ala, Asn, Cys, Gln, Ile, Leu, Met, Phe, Pro, Ser, Thr, Trp, Tyr, Val or a non-proteinogenic amino acid, and wherein in positions 1, 2, 28, 29 or 30, independent of one another, amino acids are optionally part of the sequence, and the N-terminus is represented by $NR_1R_2$ in which $R_1$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, $R_1$ denotes hydrogen, acetyl, trifluoroacetyl, adamantyl, Fmoc, benzyloxycarbonyl, Boc, Alloc, $C_1$–$C_6$ alkyl, $C_2$–$C_8$ alkenyl or $C_7$–$C_9$ aralkyl, and the C-terminus is represented by $COR_3$ in which $R_3$ equals $OR_4$ or $NR_4R_5$ in which $R_4$ equals hydrogen or $C_1$–$C_6$ alkyl in which $R_5$ equals hydrogen or $C_1$–$C_6$ alkyl as well as physiologically tolerated salts and esters thereof, with the proviso that at least one but at most 10 of the following modifications (a) to (o) apply to the amino acid chain:

(a) the α-amino acid in position 1 is D-His, Ala, D-Ala, Gly, Lys or D-Lys;

(b) the α-amino acid in position 2 is Ser, D-Ser, Thr, D-Thr, Ala, D-Ala, Ile, D-Ile, Val, D-Val, Leu, D-Leu, Cys, Asp, Glu, Phe, His, Lys, Met, Asn, Pro, Gln, Arg, Trp or Tyr;

(c) the α-amino acid in position 3 is D-Glu, D-Asp, Ala or D-Ala;

(d) the amino acid in position 4 is Ala, D-Ala or β-Ala;

(e) the α-amino acid in position 5 is Ser, Tyr or Ala;

(f) the α-amino acid in position 6 is Ala, Ile, Val, Leu, Cha or Tyr;

(g) the α-amino acid in position 7 is Ala, D-Ala, Tyr, D-Tyr, Ser, D-Ser or D-Thr;

(h) the α-amino acid in position 8 is Ala, Tyr or Thr;

(i) the α-amino acid in position 9 is Ala, D-Ala, Glu, D-Glu or D-Asp;

(j) the amino acids in positions 10, 11, 12, 15, 16, 17, 18, 19, 20, 21, 24, 28, 29 are, independent of one another, one of the above-specified proteinogenic amino acids which are different from the amino acid already present in the respective position(s) in SEQ ID NO:1 or SEQ ID NO:2 or a non-proteinogenic D- or L-amino acid;

(k) the α-amino acid in position 13 is a neutral L-amino acid except Gln:

(l) the α-amino acid in position 14 is replaced by a neutral L- or D-amino acid, except Met or L-leucine;

(m) the α-amino acid in position 22 is D-Phe, Tyr, D-Tyr, Leu, D-Leu, Val, D-Val, L-Cha, D-Cha, β-1-Nal, β-2-Nal or β-1-D-Nal;

(n) the α-amino acid in position 23 is Leu, D-Leu, D-Ile, Val, D-Val, L-Cha, D-Cha, Tyr, D-Tyr, Phe or D-Phe; and (o) the α-amino acid in positions 25, 26 or 27 is a neutral L- or D-amino acid, except Trp for position 25, Leu for position 26 and Lys for position 27.

35. A peptide as claimed in claim 34, wherein in SEQ ID NO:1 or SEQ ID NO:2 an amino acid has been substituted at position 2.

36. A peptide as claimed in claim 34, wherein in SEQ ID NO:1 or SEQ ID NO:2 an amino acid has been substituted at position 14.

37. A peptide as claimed in claim 34, wherein in SEQ ID NO:1 or SEQ ID NO:2 an amino acid has been substituted at position 3.

38. A peptide as claimed in claim 34, wherein in SEQ ID NO:1 or SEQ ID NO:2 the α-amino acid in position 1 is Ala, Gly or Lys.

39. A peptide as claimed in claim 34, wherein in SEQ ID NO:1 or SEQ ID NO:2 the α-amino acid in position 2 is Thr, Ala, Val, Ile or Leu.

40. A peptide as claimed in claim 34, wherein in SEQ ID NO:1 or SEQ ID NO:2 the α-amino acid in position 3 is Ala.

41. A peptide as claimed in claim 34, wherein in SEQ ID NO:1 or NO.2 the α-amino acid in position 4 is Ala.

42. A peptide as claimed in claim 34, wherein in SEQ ID NO:1 or SEQ ID NO:2 the α-amino acid in position 6 is Ala, Ile, Val, Leu or Tyr.

43. A peptide as claimed in claim 34, wherein in SEQ ID NO:1 or SEQ ID NO:2 the α-amino acid in position 7 is Ala, Tyr or Ser.

44. A peptide as claimed in claim 34, wherein in SEQ ID NO:1 or SEQ ID NO:2 the α-amino acid in position 9 is Ala or Glu.

45. A peptide as claimed in claim 34, wherein in SEQ ID NO:1 or SEQ ID NO:2 the α-amino acid in positions 10, 11, 12, 15, 16, 17, 18, 19, 20, 21, 24, 28, 29 is a proteinogenic L-amino acid.

46. A peptide as claimed in claim 34, wherein in SEQ ID NO:1 or SEQ ID NO:2 the α-amino acid in position 13 is a neutral proteinogenic L-amino acid.

47. A peptide as claimed in claim 34, wherein in SEQ ID NO:1 or SEQ ID NO:2 the α-amino acid in position 14 is Nle, D-Nle, Ala, D-Ala, Ile, D-Ile, Val or D-Val.

48. A peptide as claimed in claim 34, wherein in SEQ ID NO:1 or SEQ ID NO:2 the α-amino acid in position 14 is Ile, Val or Ala.

49. A peptide as claimed in claim 34, wherein in SEQ ID NO:1 or SEQ ID NO:2 the α-amino acid in position 22 is Tyr, Leu or Val.

50. A peptide as claimed in claim 34, wherein in SEQ ID NO:1 or SEQ ID NO:2 the α-amino acid in position 23 is Leu, Val, Tyr or Phe.

51. A peptide as claimed in claim 34, wherein in SEQ ID NO:1 or SEQ ID NO:2 the α-amino acid in positions 25, 26 or 27 is a proteinogenic L-amino acid.

52. A peptide as claimed in claim 34 wherein the α-amino acid in position 30 is Arg or Tyr.

53. A method of stimulating the release of insulin in a mammal comprising administering to the mammal a peptide according to claim 28 in an amount sufficient to release insulin.

54. The method of claim 53, wherein the mammal is a human.

* * * * *

UNITED STATES PATENT AND TRADEMARK OFFICE
CERTIFICATE OF CORRECTION

PATENT NO. : 6,767,887 B1
DATED : July 27, 2004
INVENTOR(S) : Eike Hoffmann et al.

It is certified that error appears in the above-identified patent and that said Letters Patent is hereby corrected as shown below:

Title page,
Item [30], should read:
-- Foreign Application Priority Data:

July 15, 1997 (Germany) 196 22 502.7
July 15, 1997 (Germany) 196 37 230.5 --

Signed and Sealed this

Twenty-sixth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,767,887 B1
DATED : July 27, 2004
INVENTOR(S) : Eike Hoffmann et al.

It is certified that error appears in the above-identified patent and that said Letters Patent is hereby corrected as shown below:

<u>Title page,</u>
Item [30], Foreign Application Priority Data, should read:
-- June 5, 1996 (Germany) 196 22 502.7
   September 13, 1996 (Germany) 196 37 230.5 --

Signed and Sealed this

Twenty-second Day of March, 2005

JON W. DUDAS
*Director of the United States Patent and Trademark Office*